United States Patent [19]

Sprecker et al.

[11] Patent Number: 4,863,631

[45] Date of Patent: Sep. 5, 1989

[54] DIMETHYL SUBSTITUTED ALKYL NITRILES, PERFUME AND BLEACH COMPOSITIONS CONTAINING SAME ORGANOLEPTIC USES THEREOF AND PROCESS INTERMEDIATES FOR PRODUCING SAME

[75] Inventors: Mark A. Sprecker, Sea Bright; Margo Androulakis, Palisades Park, both of N.J.

[73] Assignee: International Flavors & Fragrances Inc., New York, N.Y.

[21] Appl. No.: 210,935

[22] Filed: Jun. 24, 1988

[51] Int. Cl.$^4$ .............................................. C11D 7/18
[52] U.S. Cl. ................... 252/174.11; 252/95; 252/102; 252/187.23; 252/187.25; 252/547; 252/558; 252/173; 252/DIG. 14; 512/6
[58] Field of Search ...................... 252/174.11, 94, 95, 252/102, 187.23, 187.25, 547, 558, 173, DIG. 14; 512/6; 658/448; 564/268; 558/467

[56] References Cited

U.S. PATENT DOCUMENTS

| Re. 27,332 | 4/1972 | Somerville, II et al. | 252/522 |
|---|---|---|---|
| 3,265,739 | 8/1966 | Blumenthal | 260/586 |
| 3,325,369 | 6/1967 | Somerville et al. | 167/94 |
| 3,655,722 | 4/1972 | Mitchell et al. | 260/465.9 |
| 3,876,551 | 4/1975 | Laufer et al. | 252/98 |
| 4,052,194 | 10/1977 | Wilcox | 564/268 |
| 4,277,377 | 7/1981 | Webb et al. | 512/6 |
| 4,579,680 | 4/1986 | Sell | 512/6 |
| 4,772,411 | 9/1988 | Sprecker et al. | 252/174.11 |

FOREIGN PATENT DOCUMENTS

1085862  3/1976  Canada.
7608847  2/1977  Netherlands.

OTHER PUBLICATIONS

Bielstein, vol. II, 355–357, at p. 153, lines 3 and 4 and E III 2, pp. 852 and 854 [p. 853, lines 1 and 2].
DeSimone, "Perfumer & Flavorist International", vol. 4, No. 6, 1980, Allured Publishing Corp., Nitriles in Perfumery.
Arctander, Perfume & Flavor Chemicals (Aroma Chemicals), vols. I and II, 1969, Monographs 764, 839, 1121, 1451 and 2292.

Primary Examiner—Paul R. Michl
Assistant Examiner—Hoa Van Le
Attorney, Agent, or Firm—Arthur L. Liberman

[57] ABSTRACT

Described are dimethyl substituted alkyl nitriles of our invention defined according to the generic structure:

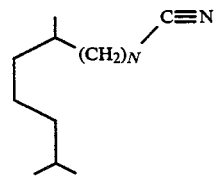

wherein N represents 0 or 1 and organoleptic uses thereof in augmenting or enhancing the aroma of perfume compositions, colognes and perfumed articles including but not limited to bleach compositions, solid or liquid anionic, cationic, nonionic or zwitterionic detergents, perfumed polymers, fabric softener compositions, fabric softener articles, cosmetic powders and hair preparations.

Also described is a process for preparing such dimethyl substituted alkyl nitriles of our invention by means of reaction of aldehydes defined according to the structure:

(Abstract continued on next page.)

GLC PROFILE FOR EXAMPLE I.

4,863,631
Page 2
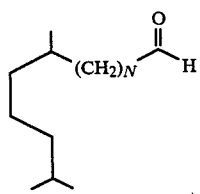
with hydroxylamine salts having the structure:
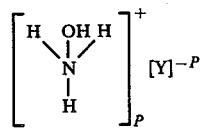
wherein Y is an anion and P is 1 or 2 to form aldoximes defined according to the structure:
The compounds defined according to the generic structure:
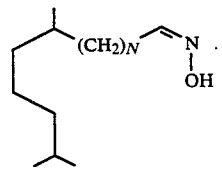
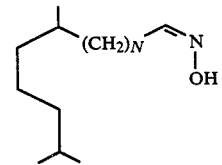
are novel compounds.
17 Claims, 10 Drawing Sheets

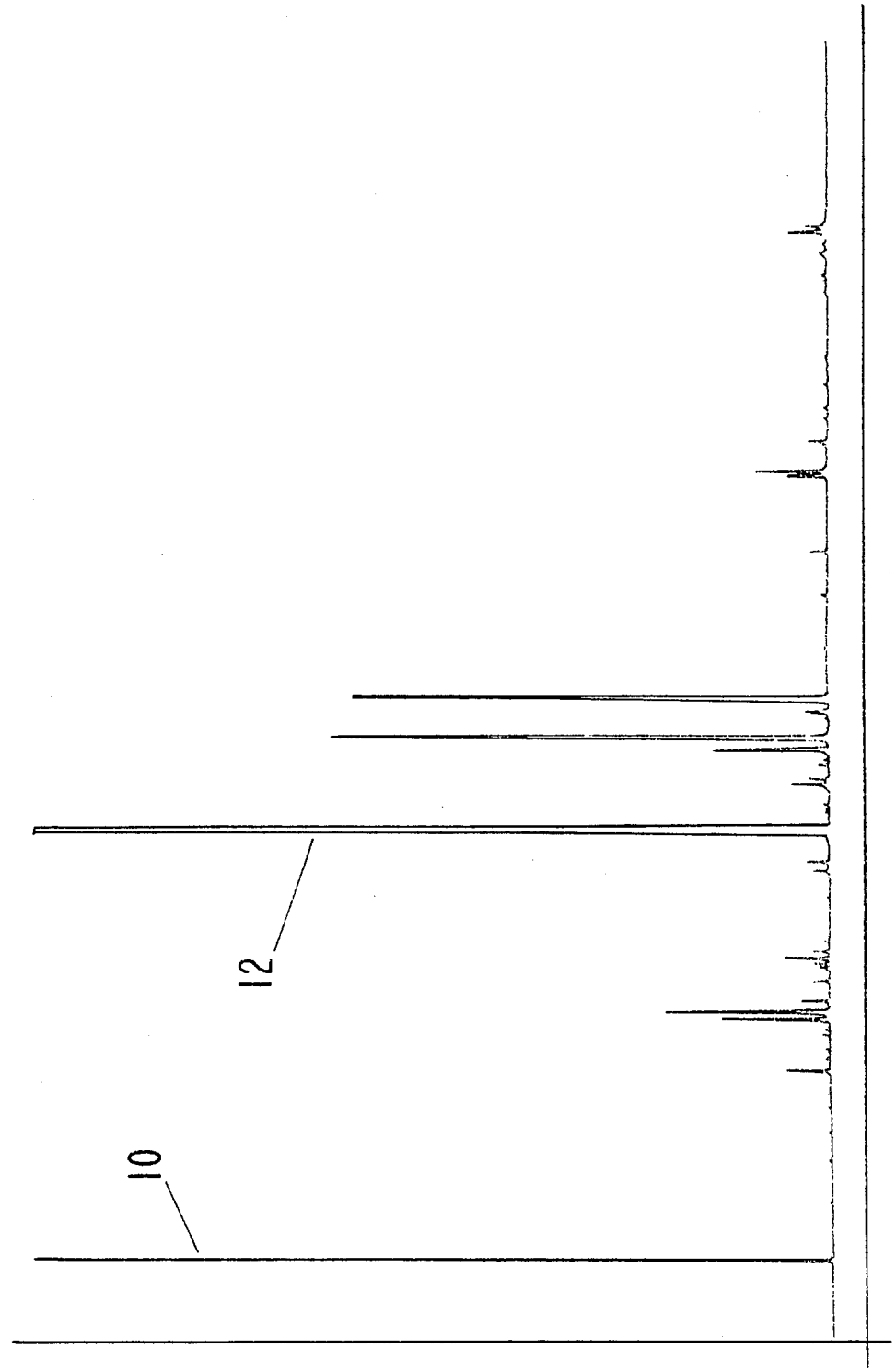

GLC PROFILE FOR EXAMPLE II.

GLC PROFILE FOR EXAMPLE III.
CRUDE

GLC PROFILE FOR EXAMPLE III.

FIG.5 NMR SPECTRUM FOR EXAMPLE III.

FIG. 6 NMR SPECTRUM FOR EXAMPLE IV.

GLC PROFILE FOR EXAMPLE V.
OXIME INTERMEDIATE

GLC PROFILE FOR EXAMPLE V.
NITRILE PRODUCT

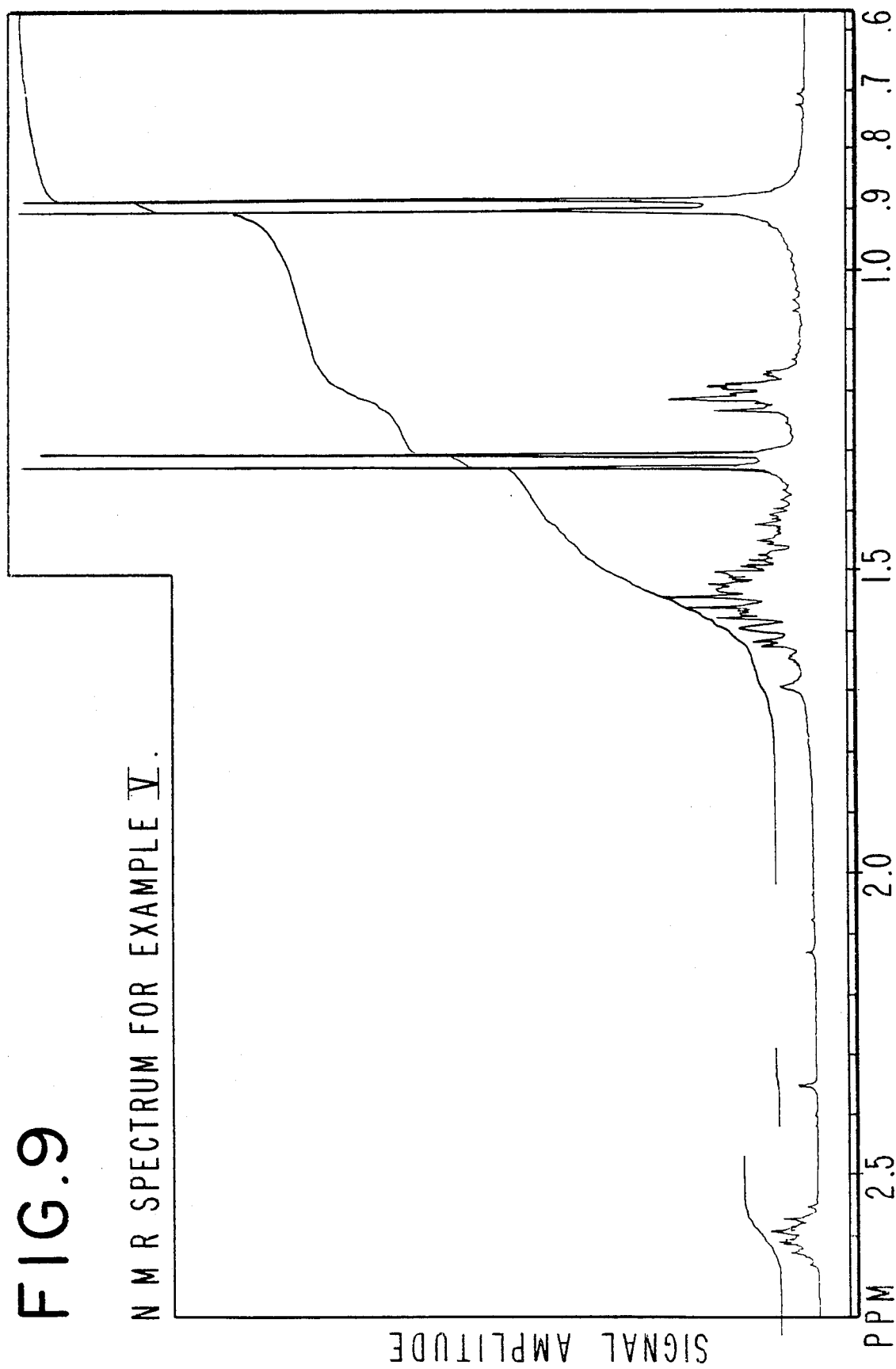

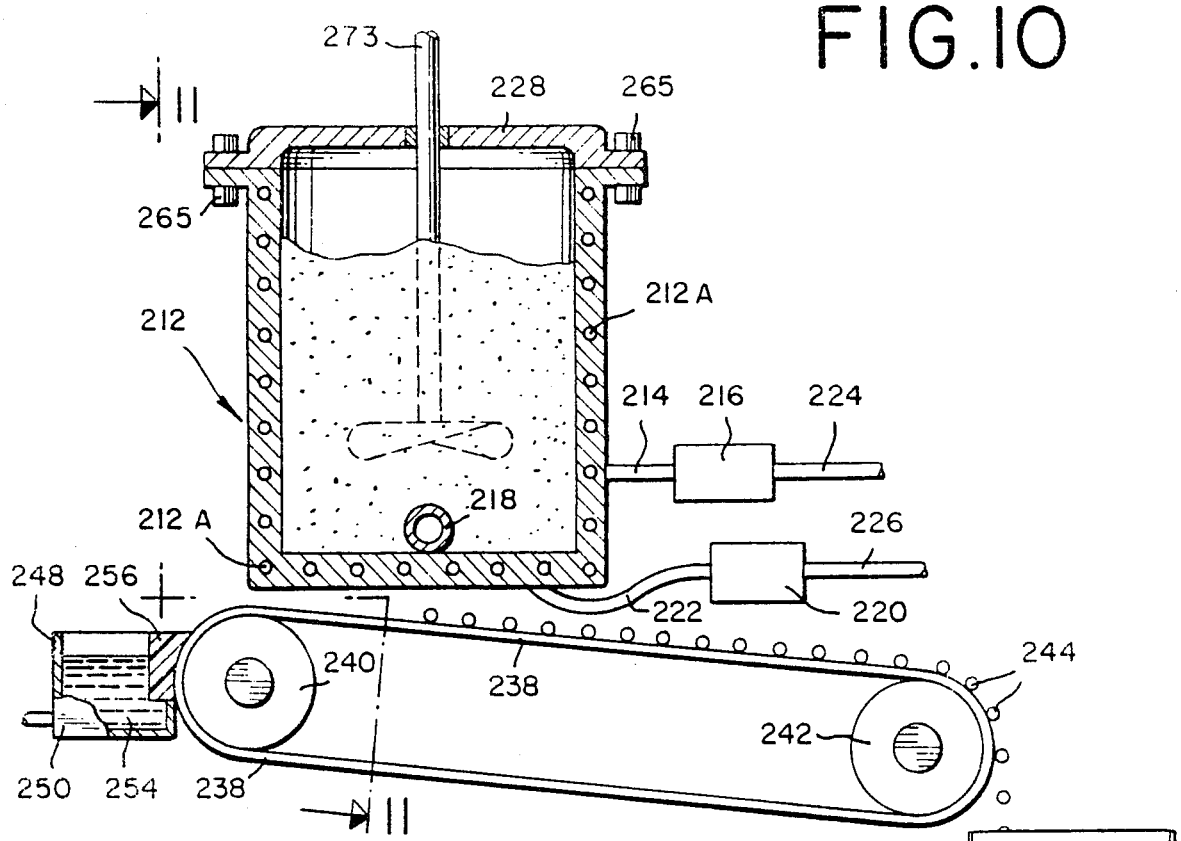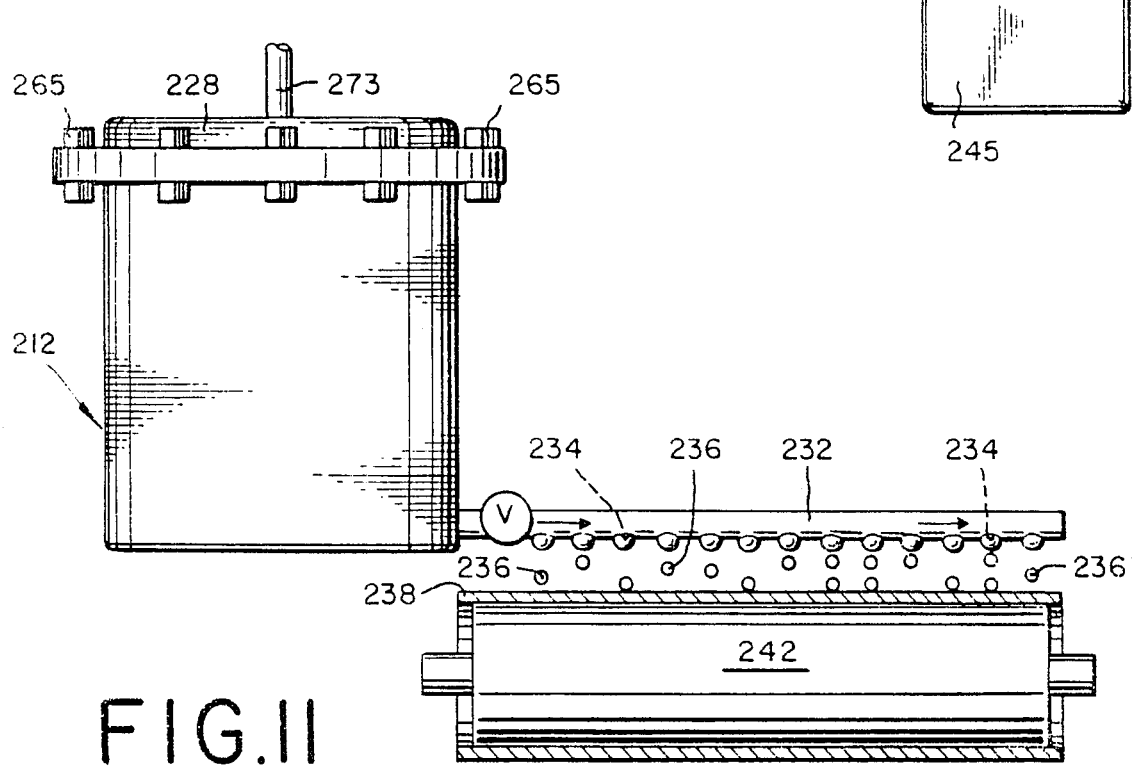

DIMETHYL SUBSTITUTED ALKYL NITRILES, PERFUME AND BLEACH COMPOSITIONS CONTAINING SAME ORGANOLEPTIC USES THEREOF AND PROCESS INTERMEDIATES FOR PRODUCING SAME

BACKGROUND OF THE INVENTION

The present invention relates to dimethyl substituted alkyl nitriles of our invention defined according to the generic structure:

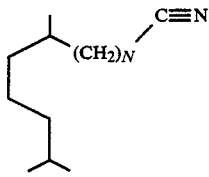

wherein N represents 0 or 1 and uses thereof to alter, modify or enhance the aroma of consumable materials.

There has been considerable work performed relating to substances which can be used to impart (modify, augment or enhance) fragrances to (or in) various consumable materials. These substances are used to diminish the use of natural materials, some of which may be in short supply and to provide more uniform properties in the finished product.

Long-lasting and substantive orris-like, cinnamon-like, sweet, citrus, lemony, fatty, coconut-like, rhodinol-like, minty, geranium-like and scorched linen aromas with floral undertones are desirable in several types of perfume compositions, perfumed articles and colognes.

Furthermore, considerable difficulties have heretofore been encountered in using compounded hypochlorite bleach or sterilizing solutions with perfume oils so that a stable long-lasting, single phase commercially feasible bleach or sterilizing solution has been difficult to obtain, particularly wherein the desired aroma of the article bleached or sterilized (e.g., clothing) has a pleasant and stable and consistent aroma on drying (and not the usual "hypochlorite-bleached-article" aroma). The problem has been defined in United Kingdom patent specification No. 886,084 published on Jan. 3, 1962 wherein it is stated that a stable "dispersion" of hypochlorite-resistant perfume in aqueous solutions of hypochlorites was formulated. United Kingdom patent specification No. 886,084 discloses the preparation of an aqueous "solution" of a hypochlorite containing a hypochlorite resistant perfume and a surface active quaternary ammonium compound of the betaine type soluble in the hypochlorite solution. Such ammonium compounds have the generic structure:

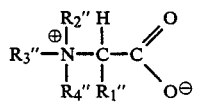

wherein each of $R_1''$, $R_2''$, $R_3''$ and $R_4''$ are alkyl. One of the features of the perfumed solutions produced in accordance with said United Kingdom patent specification No. 886,084 is indicated to be that the solution exhibits foaming properties. Another feature of United Kingdom patent specification No. 886,084 is stated to be that the perfumed solutions covered by the patent are found to be clear and homogeneous after eight weeks of storage at room temperature. Nevertheless, betaines such as "Ambiteric D" as are discussed therein are not so broadly useful when used in concentrations of from 0.15% up to 4.0% (based on total weight of bleach or sterilizing solution) as to have the ability to be used in conjunction with perfume oils which should be incorporated into thickened, high viscous hypochlorite bleaches or sterilizers having excellent surface tension properties so that long lasting stable soluble single phase thickened perfumed aqueous alkali metal hypochlorite bleach or sterilizing solutions having long lasting pleasant stable aromas are obtained, particularly where the quantity of perfume oil in the bleach or sterilizing substance is at levels of between 0.02% and 0.8% by weight of the total bleach or sterilizing solution. The need for such aromas (e.g., "citrusy") to be present in such bleach or sterilizing solutions exists so that the disagreeable characteristic "hypochlorite" aroma is substantially eliminated from aromas of the product to which the bleach or sterilizing solution is applied; particularly on dry-out, as well as from the aroma of the hands of the user when they are in direct contact with such bleach or sterilizing solutions.

U.S. Pat. No. 3,560,389 also discloses the feasibility of using perfume oils in hypochlorite bleaches or sterilizers at column 3, lines 37–40 but the disclosure is limited to inclusion of various detergents in addition to amine oxides, such as lithium lauryl sulfate and sodium lauryl ether sulfate and/or is further limited to include hydrotropes such as sodium xylene sulfonate in addition to the amine oxide. Exclusion of such hydrotropes and detergents additional to the amine oxides and diphenyl oxide derivatives is desirable not only to cause the dimethyl substituted alkyl nitriles of our invention to function properly, but also from an ecological standpoint.

European Chemical News, Volume 13, Jan. 18, 1968, sets forth a synopsis of South African Pat. No. 67/4667 which corresponds to U.S. Pat. No. 3,560,389, but the reference also states at page 42:

"Alternatively, a detergent with bleaching or bacteriocidal properties can be formulated. Perfuming bleaching solutions is now possible."

Neither the South African nor the United States Patents, however, indicate the advantages and usefulness of limiting the detergents either to (a) compounds having the generic structure:

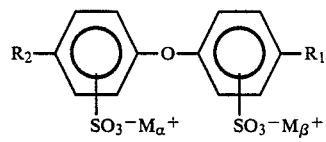

wherein at least one of $R_1$ and $R_2$ represents $C_{10}$–$C_{12}$ straight chain or branched chain alkyl and when one of $R_1$ or $R_2$ is $C_{10}$–$C_{12}$ branched or straight chain alkyl, the other of $R_1$ or $R_2$ is pH-adjusted hydrogen and wherein $M_\alpha$ and $M_\beta$ are the same or different and each represents alkali metal which may be sodium, lithium or potassium, or (b) to mixtures of compounds having the structure:

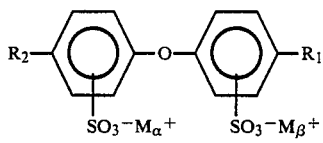

with at least one amine oxide defined according to the structure:

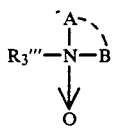

of excluding from the formulation a hydrotrope or of specifying the nature of the perfume oil useful in the perfumed bleach or sterilizing solution (wherein A and B are each separately methyl or taken together, complete a morpholino ring and wherein $R_3'''$ is straight chain alkyl having from 11 up to 13 carbon atoms).

U.S. Pat. No. 3,876,551, in attempting to solve the foregoing problem discloses a stable single phase aqueous alkali metal hypochlorite liquid perfume bleach or sterilizing composition comprising an aqueous mixture of (1) an amine oxide composition consisting essentially of at least one morpholino- and/or dimethyl ($C_{11}-C_{13}$ straight chain alkyl) amine oxide in an amount greater than 55% of said amine oxide composition, (2) at least one alkali metal hydroxide, (3) at least one alkali metal hypochorite, and (4) a perfume oil compatible with the mixture capable of imparting a "woody" or a "floral" or a "clean fresh" or a "citrusy" note to the bleach or sterilizing composition; the mixture having a pH in the range of from 12 to 13.5 and the mixture excluding hydrotropes as well as all surfactants except the amine oxide.

Included in the perfume compositions of U.S. Pat. No. 3,876,551 are:

(i) at column 6, lines 5 and 6: long chain aliphatic nitriles such as n-dodecyl nitriles; and
(ii) at column 6, line 29: n-undecyl nitrile.

U.S. Pat. No. 3,876,551 also attempts to solve the foregoing problem by setting forth a process for producing the above-named mixture comprising the steps of combining an amine oxide composition consisting essentially of one or more morpholino and/or dimethyl $C_{11}-C_{13}$ straight chain alkyl amine oxide(s) with the perfumed oil to form an amine oxide-perfume oil premix; admixing the amine oxide-perfumed oil premix with an aqueous alkali metal hypochlorite solution, and combining the alkali metal hydroxide with the solution whereby the final pH of the mixture is from 12 up to 13.5. In a further effort to solve the foregoing problem U.S. Pat. No. 3,876,551 also discloses adjustment of the pH of the aqueous metal hypochlorite solution initially to the range of 12-13.5 and then combining the resulting aqueous hypochlorite solution with the aforementioned premix. The resulting composition is indicated to cause products to which said composition is applied to have eliminated therefrom the disagreeable characteristics "hypochlorite" aroma and instead to have a "clean fresh" or "floral" or "woody" or "citrusy" aroma to be imparted to the treated products. In addition, it is stated that the hands of the individual user after using and being in direct contact with the hypochlorite composition will not have the disagreeable characteristics "hypochlorite" aroma but instead will have a pleasant "clean fresh" or "floral" or "woody" or "citrusy" aroma.

The disadvantage of the system of U.S. Pat. No. 3,876,551 however, concerns (a) the inability to use a thickener in the system whereby the resulting liquid has a viscosity of 5-25 centipoises at 20°-40° C. and (b) the relatively low degree of chemical stability and substantive stability of the perfume oil and of the single liquid phase system. Nothing in U.S. Pat. No. 3,876,551 indicates such a high degree of stabilities of the perfume-hypochlorite system as exists in the system of the present invention; wherein there is also included a thickener. Indeed, the stabilities using the system of the instant invention are far greater even at levels as low as 3% hypochlorite and are also relatively stable (from a standpoint of chemical stability of perfume oil, substantive stability of perfume oil and phase separation stability taken in combination with one another) at levels of as high as 10% hypochlorite in aqueous solution. Thus, the instant system gives rise to unexpected, unobvious and advantageous properties over the systems taught in the prior art.

Furthermore, nothing in the prior art including the teaching of U.S. Pat. No. 3,876,551 states either explicitly or implicitly the compatability of a thickener in the instant system, such as sodium palmitate, sodium stearate, potassium palmitate, potassium stearate, lithium palmitate, lithium stearate, lithium laurate, potassium laurate or sodium laurate whereby a stable gel (as opposed to a liquid) phase perfumed hypochlorite system or perfumed oil stabilizer emulsifier system "premix" may be produced.

The combination of the compound group having the structure:

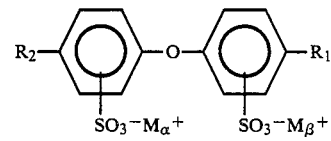

(wherein $R_1$, $R_2$, $M_\alpha$ and $M_\beta$ are defined, supra) with perfume and hypochlorite bleach in general, is set forth in the Kao Soap Company, Japanese Patent No. 25514/79 filed on Nov. 2, 1973 and opened for public inspection on June 19, 1975. Thus, on page 2, at column 4, line 15, the compound:

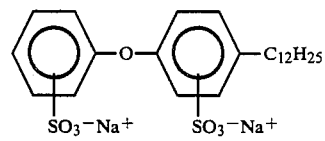

is disclosed for use in conjunction with the perfumed hypochlorite bleaches. The claim of the Kao Soap Patent is as follows:

Claim: An aromatic liquid bleaching composition containing, as active ingredient, sodium hypochlorite, which comprises one or more of simple perfumes or compounded perfumes selected from the group consisting of anisole, benzophenone, benzylphenyl ether, bromelia, cedrenyl acetate, p-tertiary butylcyclohexanol, dimethylbenzylcarbinyl acetate, dihydroterpinyl acetate, diphenyl oxide, dimethylbenzylcarbinol, dimethylphenylcarbinol, dihydroterpineol, fenchyl acetate, fenchyl alcohol, p-methyldimethylbenzylcarbinol, methylphenylcarbinyl acetate, methyl-n-valerate, muskmoskene, muscarone, methylamyl ketone, phenylethyldimethylcarbinyl acetate, rose phenone, styrallyl propionate, tetrahydromuguol, tetrahydromugyl acetate, tetrahydrolinalool, tetrahydrolinalyl acetate, verool, velveton, verdox, coniferan and yara yara, and a surface active agent which can stably be dissolved in an aqueous solution of sodium hypochlorite.

Furthermore, the use of such compounds as those having the structure:

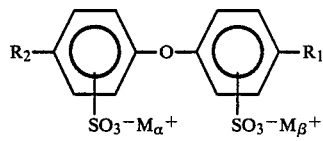

(wherein $R_1$, $R_2$, $M_\alpha$ and $M_{62}$ have been previously defined) with hypochlorite bleaches is documented in the brochure of Dow Chemical entitled "DOWFAX Surfactants" and is covered in the Dow Chemical Company Pat. No. 3,172,861 issued on Mar. 9, 1965.

Nothing in the prior art discloses, however, the utility of the thickeners of the instant application taken together with a perfume oil (e.g., "diisoamylene" or "diisoamylene epoxide") and one of the compounds defined according to the generic structure:

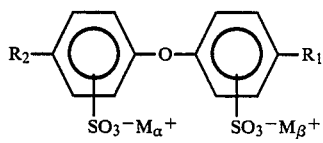

(wherein $R_1$, $R_2$, $M_{60}$ and $M_\beta$ have been defined, supra) in hypochlorite bleaches, particularly where the hypochlorite concentration is greater than 7%. More particularly, nothing in the prior art discloses the use of such systems in conjunction with a thickener such as sodium palmitate, potassium palmitate, sodium stearate, potassium stearate, sodium laurate, potassium laurate, lithium laurate, lithium stearate or lithium palmitate, whereby a stable gelled perfumed hypochlorite mixture is formed or whereby a "premix" gel-phase perfume oil-stabilizing/emulsifying agent is formed.

The dimethyl substituted alkyl nitriles of our invention are unique insofar as the aforementioned systems are concerned for use in hypochlorite bleaches. Nothing in the prior art discloses any organic compounds even remotely similar to the dimethyl substituted alkyl nitriles of our invention for use as a stable aroma augmenting or enhancing agent in hypochlorite bleaches.

However, the use of nitriles in perfumery is well known in the prior art as will be seen by reference to the following publications:

(i) U.S. Pat. No. 3,325,369 issued on June 13, 1967 and reissue Pat. No. 27332 disclose the compound having the structure:

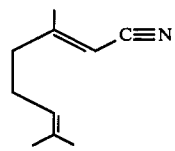

for use in perfumery;

(ii) U.S. Pat. Nos. 3,553,110 issued on Jan. 5, 1971 and 3,655,722 issued on Apr. 11, 1972 disclose the compound having the structure:

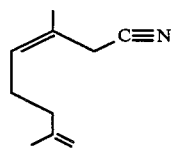

for use in perfumery.

(iii) Dutch published application No. 76/08847 discloses the compound having the structure:

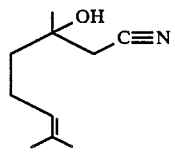

for use in perfumery;

(iv) Arctander "Perfume And Flavor Chemicals" (Aroma Chemicals) published by the author in 1969 discloses:

(a) at Monograph No. 764, the perfumery use of the compound having the structure:

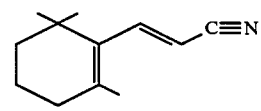

(b) at Monograph No. 839, the perfumery use of the compound having the structure:

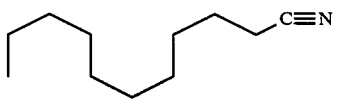

(c) at Monograph No. 1121, the perfumery use of the compound having the structure:

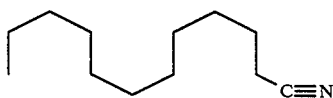

(d) at Monograph No. 2292, the perfumery use of the compound having the structure:

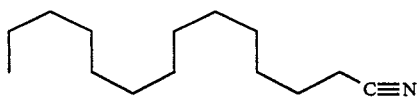

Furthermore, available to the industry is a compound entitled "MNA" nitrile having the structure:

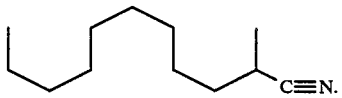

Furthermore, "Perfumer & Flavorists International" published in 1980 by Allured Publishing Corporation, Volume 4, No. 6, commencing on page 1, an article by Dr. Robert DeSimone entitled "Nitriles in perfumery" wherein a number of nitriles are disclosed as having perfumery properties.

Nothing in the prior art however discloses the perfumery use, particularly for uses in bleaches of the dimethyl substituted alkyl nitriles of our invention.

Biostein, Volume II, at page 153, discloses that the compound having the structure:

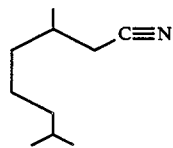

has a "citrus aroma" (translated from "Riecht Citronenartig").

The dimethyl substituted alkyl nitriles of our invention are unique with respect to hypochlorite bleach systems. Nothing in the prior art discloses any organic compounds even remotely similar to the dimethyl substituted alkyl nitriles of our invention for use as stable aroma augmenting or enhancing agents in hypochlorite bleaches. Furthermore, nothing in the prior art implies the dimethyl substituted alkyl nitriles of our invention are useful in augmenting or enhancing the aroma of perfume compositions, colognes or perfumed articles.

BRIEF DESCRIPTION OF THE DRAWINGS

FIG. 1 is the GLC profile for the reaction product of Example I, containing the compound having the structure:

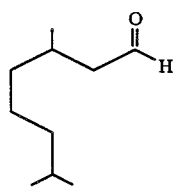

(Conditions: OV-1 column programmed at 80°–220° C. at 2° C. per minute)

Figure 2:
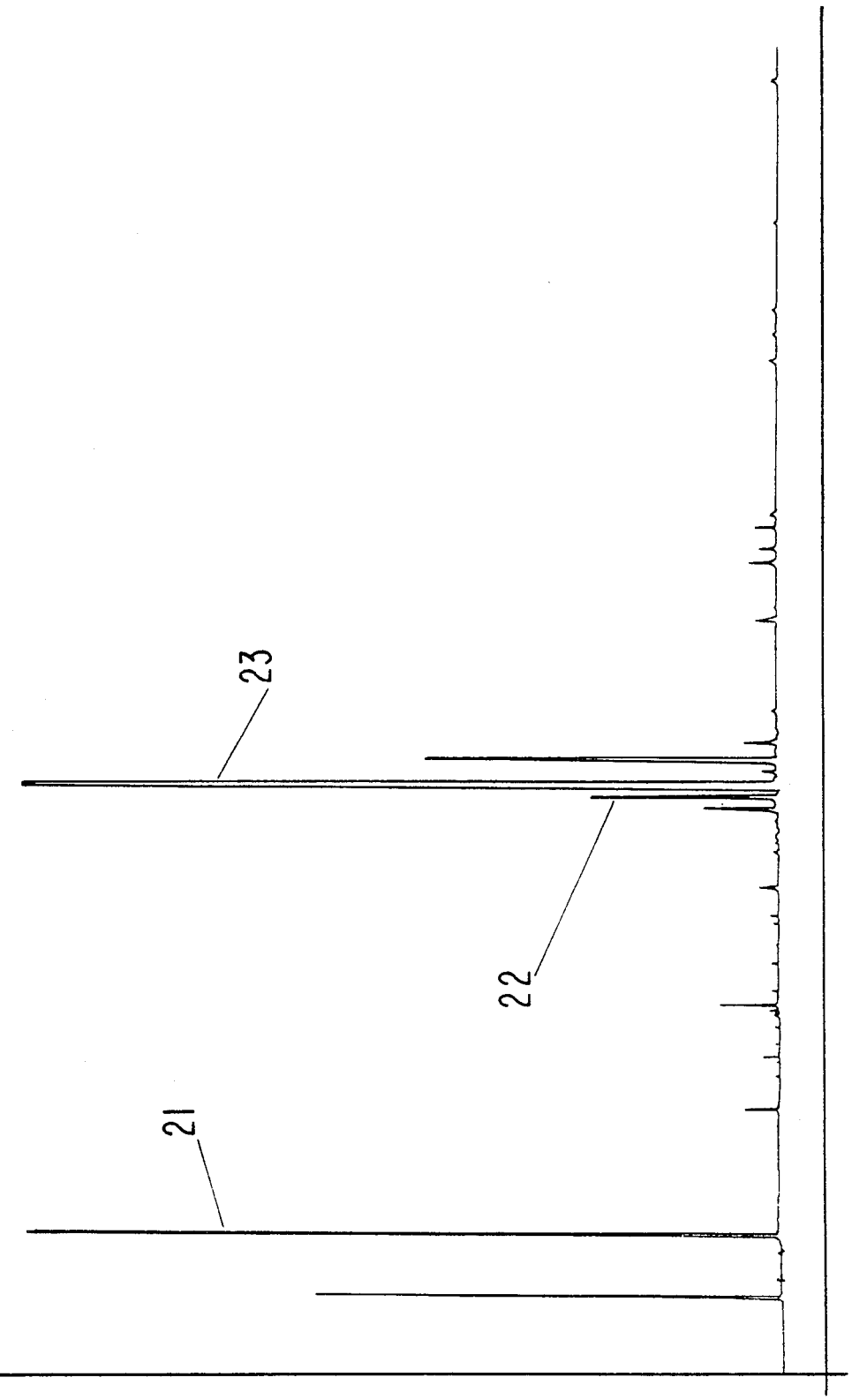

FIG. 2 is the GLC profile for the reaction product of Example II, containing the compound having the structure:

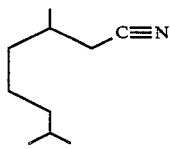

(Conditions: Methyl silicone column programmed at 80°–220° C. at 2° C. per minute).

Figure 3:
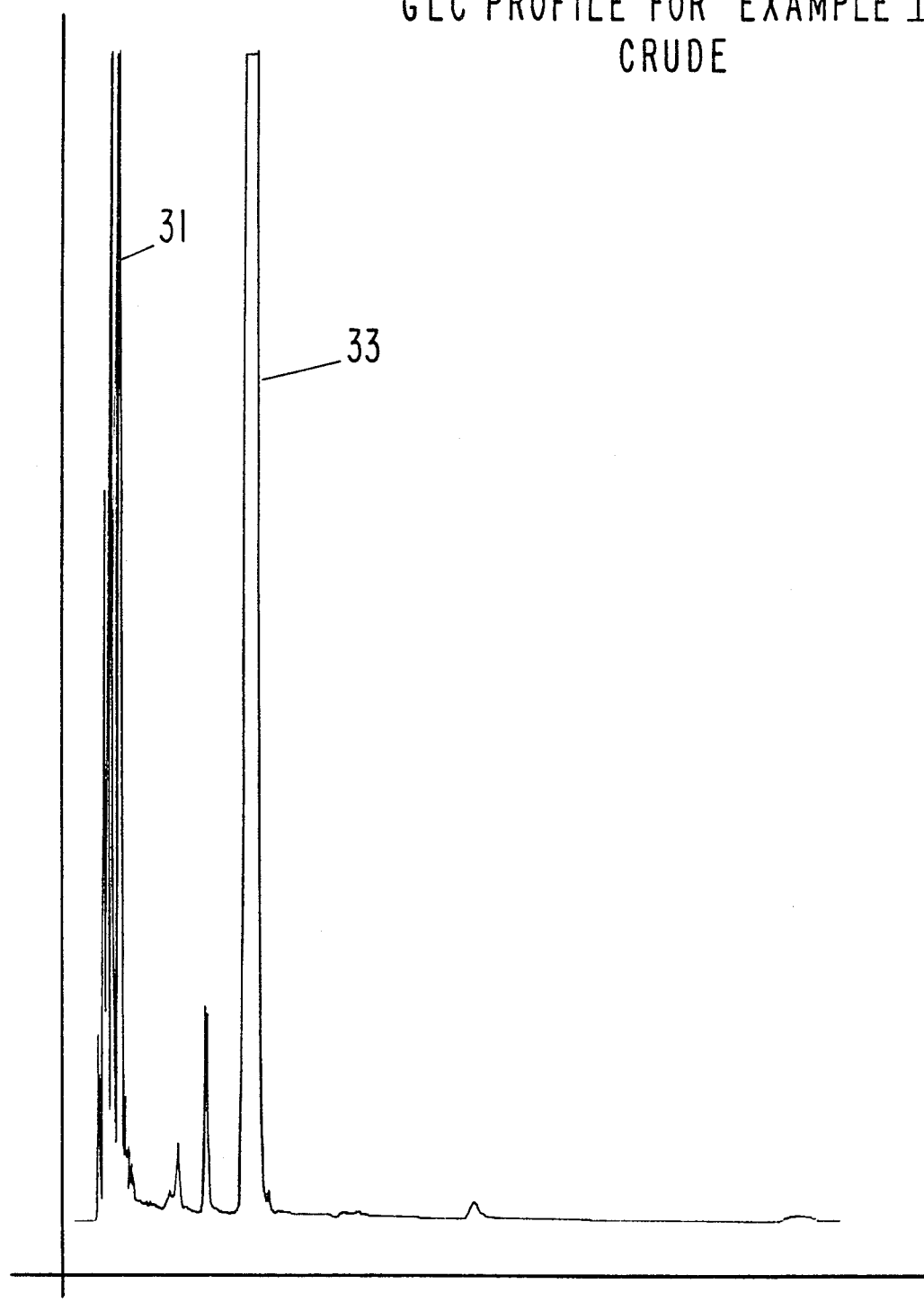

FIG. 3 is the GLC profile for the crude reaction product of Example III, containing the compound having the structure:

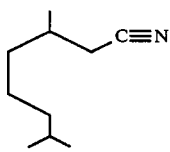

(Conditions: SE-30 column programmed at 150° C. isothermal).

Figure 4:
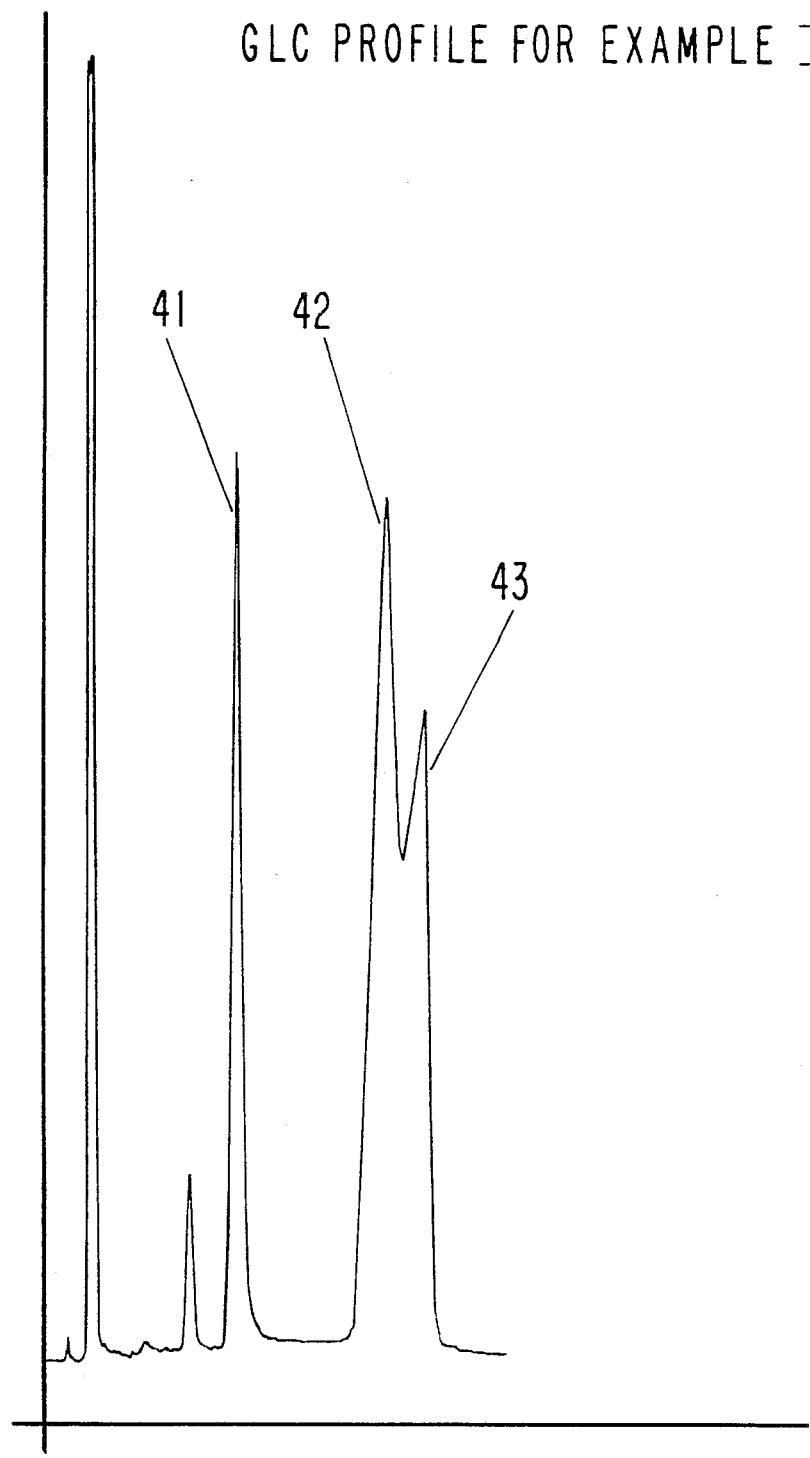

FIG. 4 is the GLC profile for the reaction product of Example III, containing the compounds having the structures:

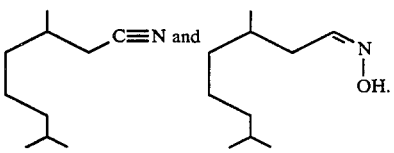

Figure 5:
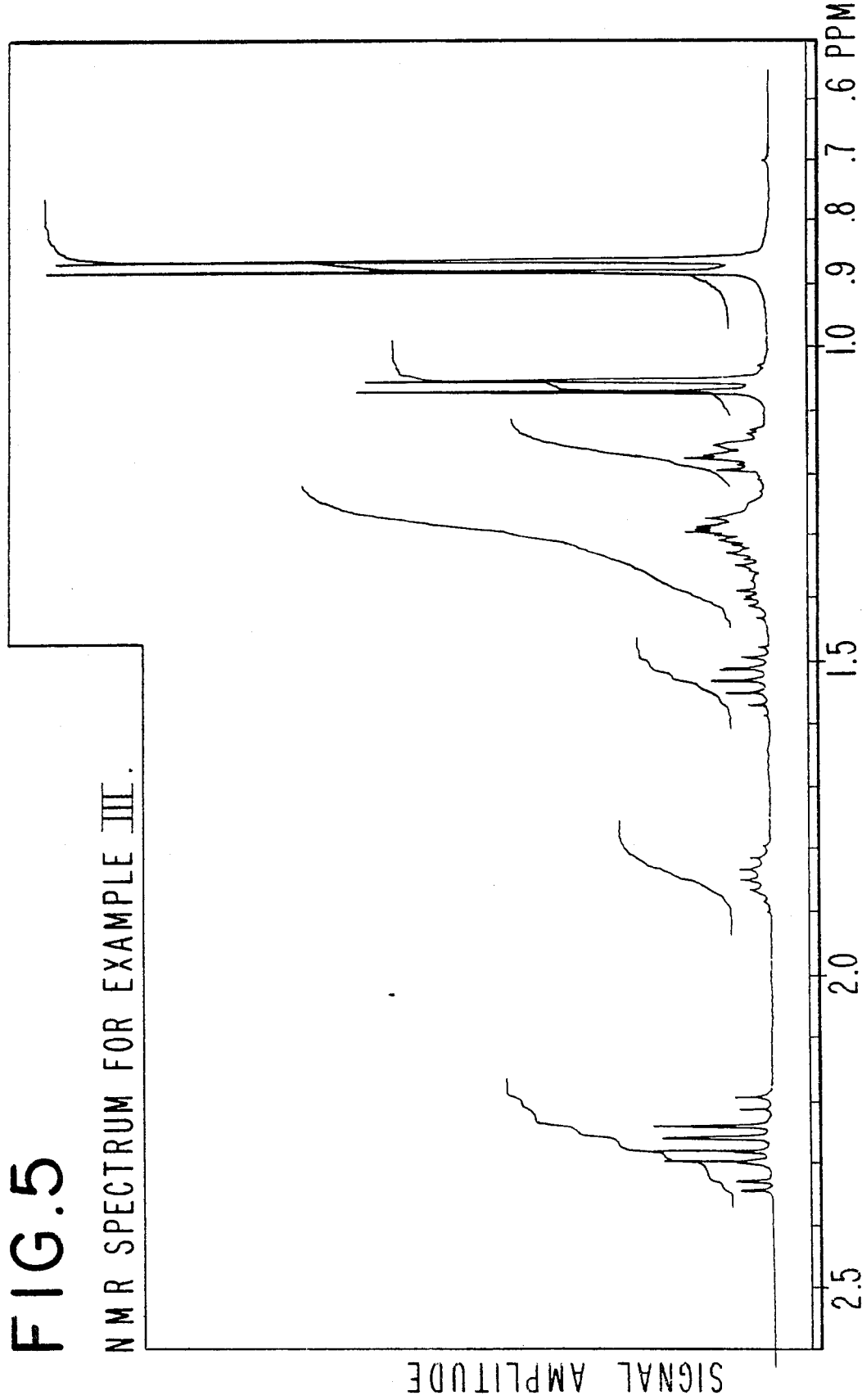

FIG. 5 is the NMR spectrum for the compound having the structure:

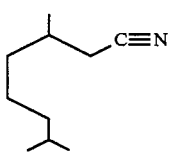

produced according to Example III.

Figure 6:
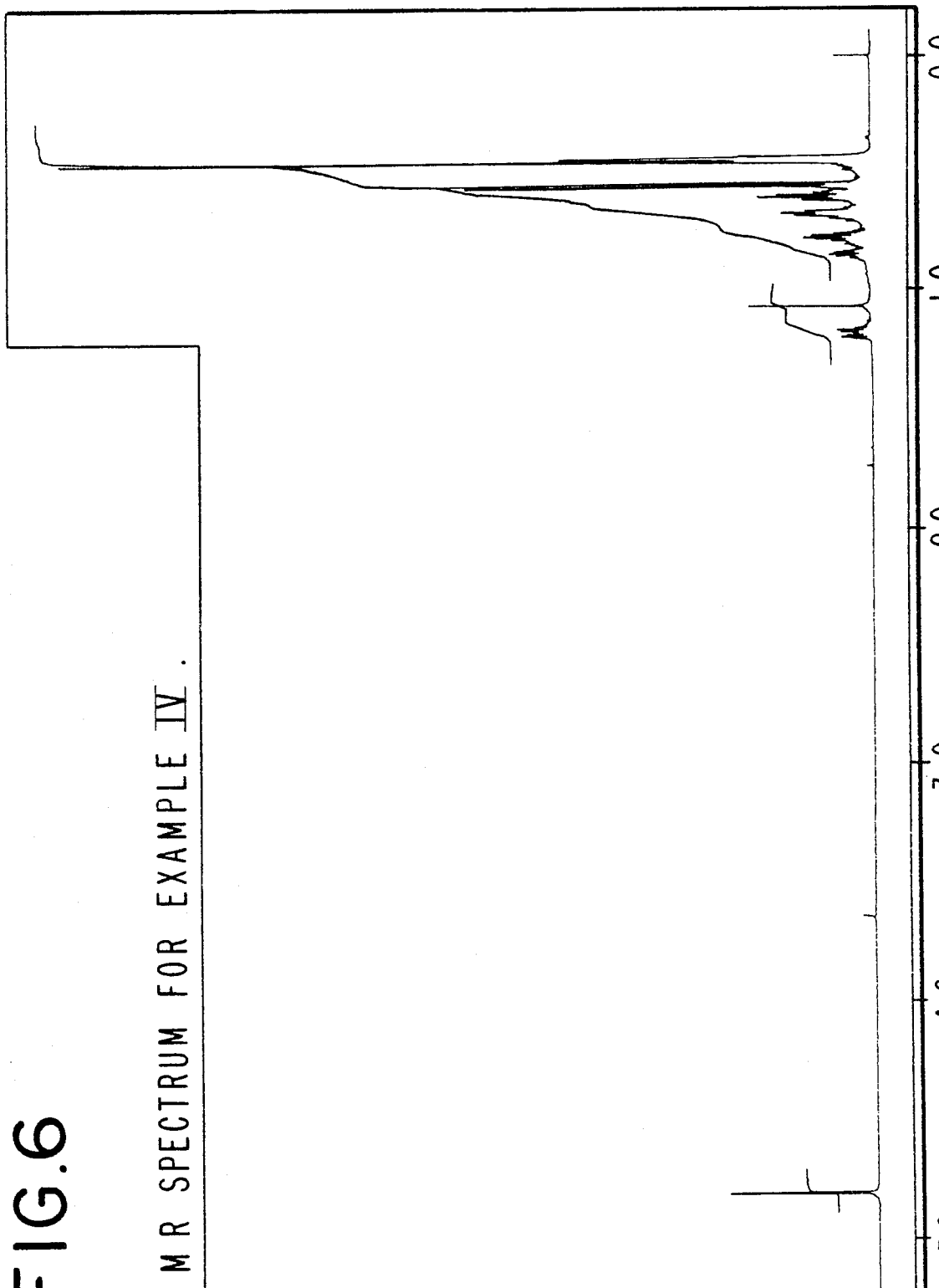

FIG. 6 is the NMR spectrum for the compound having the structure:

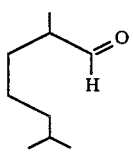

produced according to Example IV.

Figure 7:
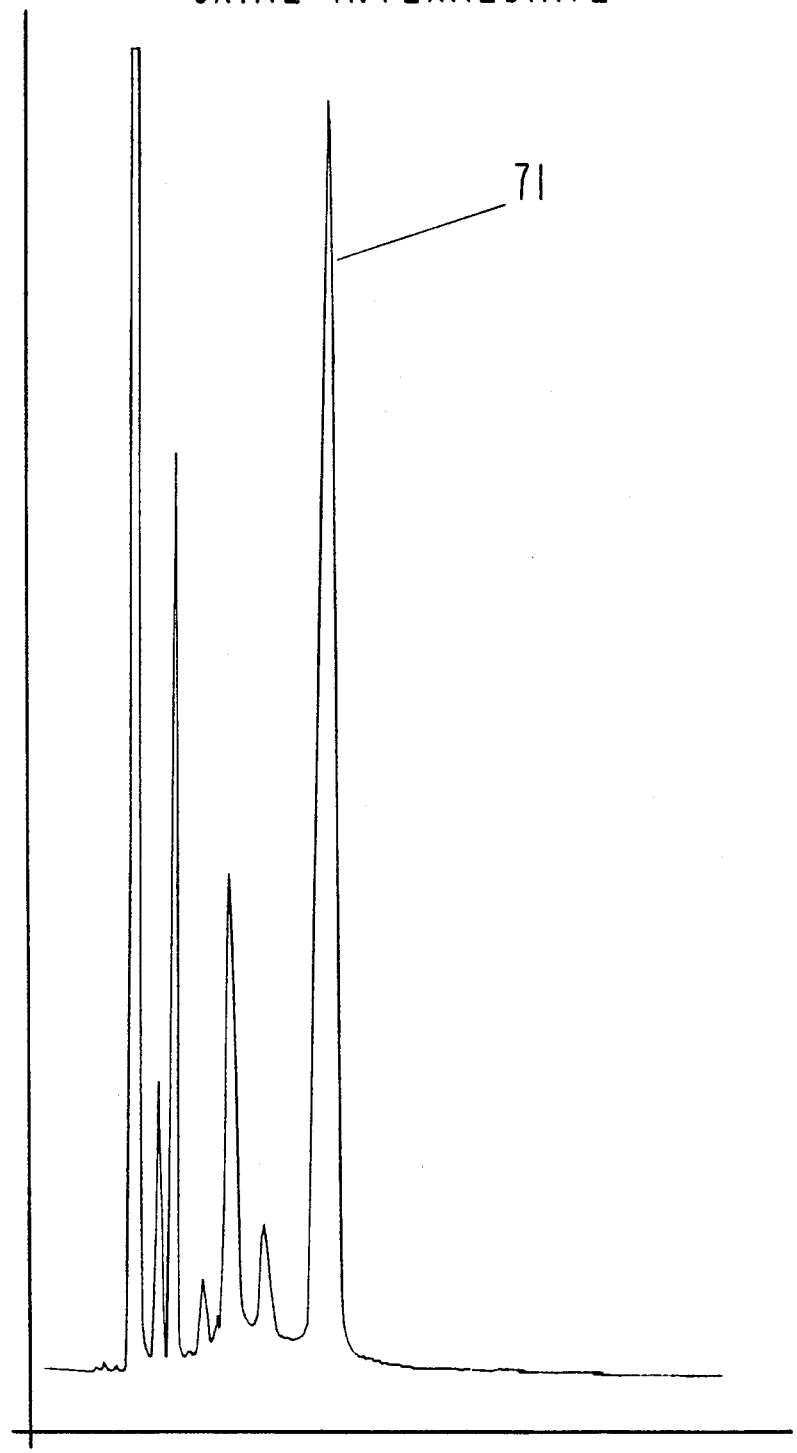

FIG. 7 is the GLC profile for the reaction product of Example V, containing the compound having the structure:

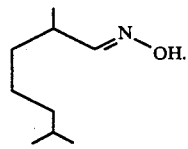

Figure 8:
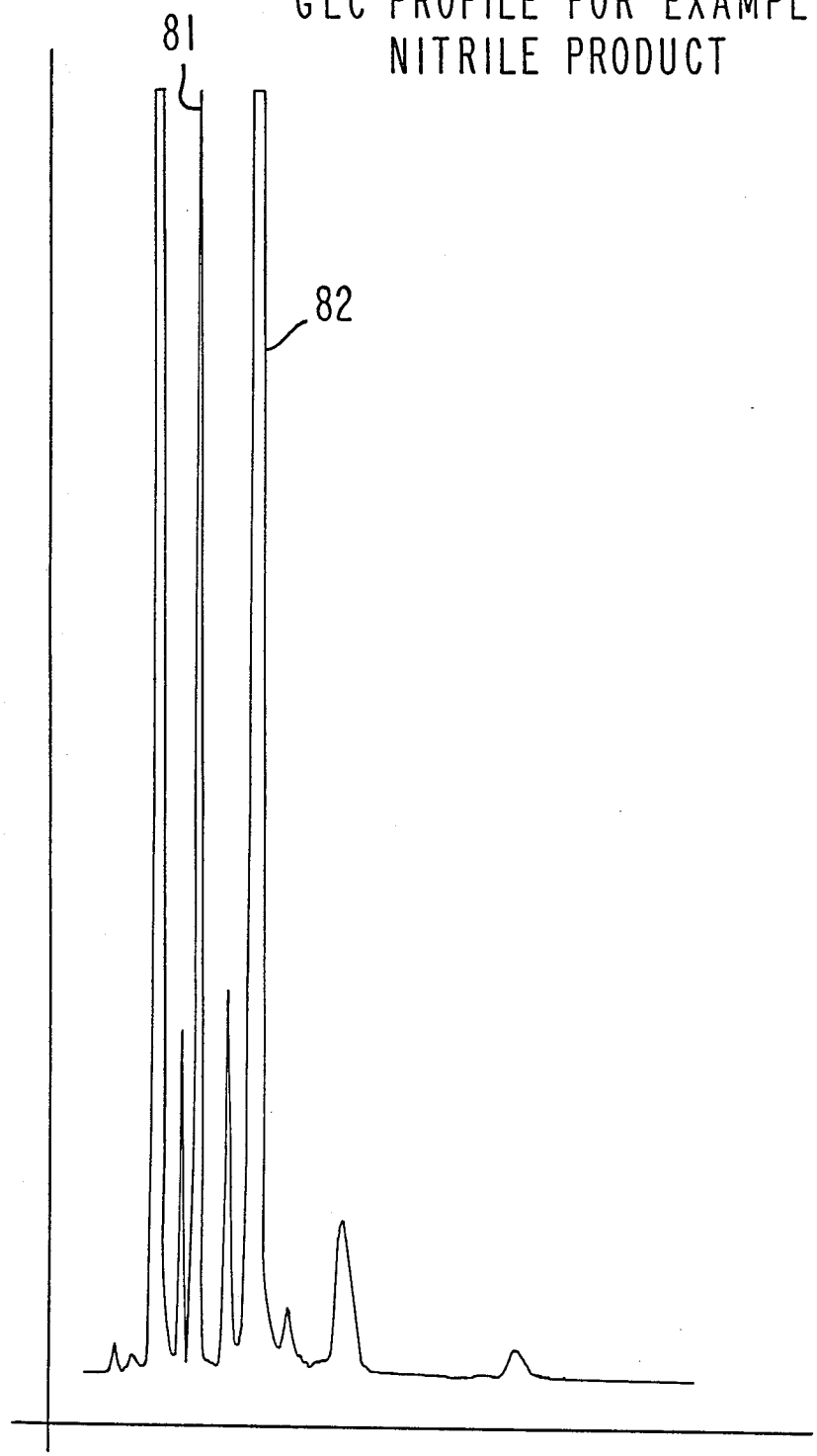

FIG. 8 is the GLC profile for the reaction product of Example V, containing the compound having the structure:

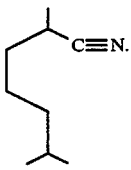

FIG. 9 is the NMR spectrum for the compound having the structure:

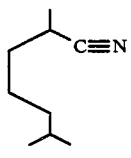

produced according to Example V.

FIG. 10 represents a cut-away side elevation view of apparatus used in forming perfumed polymers which contain imbedded therein at least one of the dimethyl substituted alkyl nitriles of our invention.

FIG. 11 is a front view of the apparatus of FIG. 10 looking in the direction of the arrows.

DETAILED DESCRIPTION OF THE DRAWINGS

FIG. 1 is the GLC profile for the reaction product of Example I (Conditions: bonded methyl silicone (OV-1) column programmed at 80°–220° C. at 2° C. per minute). The peak indicated by reference numeral 10 is the peak for the isopropyl alcohol solvent. The peak indicated by reference numeral 12 is the peak for the reaction product having the structure:

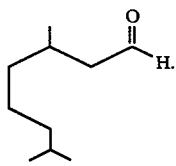

FIG. 2 is the GLC profile for the crude reaction product of Example II (Conditions: Methyl silicone column programmed at 80°–220° C. at 2° C. per minute). The peak indicated by reference numeral 21 is the peak for the toluene solvent. The peak indicated by reference numeral 22 is the peak for the compound which is a byproduct of the reaction having the structure:

The peak indicated by reference numeral 23 is the peak for the compound having the structure:

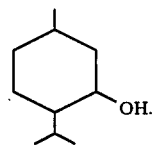

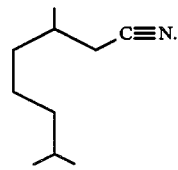

FIG. 3 is the GLC profile for the crude reaction product of Example III ((Conditions: SE-30 column programmed at 150° C. isothermal). The peak indicated by reference numeral 31 is the peak for the solvent. The peak indicated by reference numeral 33 is the peak for the reaction product which is the compound having the structure:

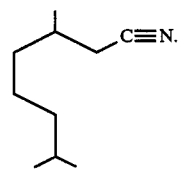

FIG. 4 is the GLC profile for the oxime intermediate reaction product of Example III. The peak indicated by reference numeral 41 is the peak for the compound having the structure:

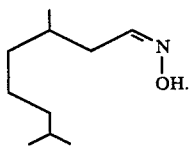

The peak indicated by reference numeral 42 and the peak indicated by reference numeral 43 are for the compound having the structure:

FIG. 7 is the GLC profile for the reaction product of Example V (Conditions: SE-30 column programmed at 180° C. isothermal). The peak indicated by reference numeral 91 is the peak for the compound having the structure:

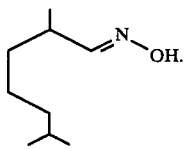

FIG. 8 is the GLC profile for the reaction product of Example V. The peak indicated by reference numeral 82 is the peak for the compound having the structure:

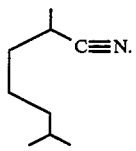

Referring to FIGS. 10 and 11, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed (and, further, which may be exposed to chlorine bleaches). This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 10 and 11, in particular, the apparatus used in producing such elements comprises a device for forming the polymer containing the perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the dimethyl substituted alkyl nitriles of our invention or mixtures of dimethyl substituted alkyl nitriles of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90-100 sayboldt seconds. The heater 218 is operated to maintain the upper portion of the container 212 within a temperature range of, for example, 220°-270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°-270° C.

Thus, the polymer or mixture of polymers added to the container 212 is heated from 10-12 hours, whereafter the perfume composition or perfume material which contains one or more of the dimethyl substituted alkyl nitriles of our invention is quickly added to the melt. Generally, about 10-45 percent by weight of the resulting mixture of the perfumery substance is added to the polymer.

After the perfume material is added to the container 212, the mixture is stirred for a few minutes, for example, 5-15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the dimethyl substituted alkyl nitriles of our invention or mixture of dimethyl substituted alkyl nitriles of our invention and one or more other substances (optionally), will continuously drop or drip through the orifices 234 downwardly from the conduit 232. During this time, the temperature of the polymer intimately admixed with the perfumery substance in the container 212 is accurately controlled so that a temperature in the range of from about 240°-250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains one or more of the dimethyl substituted alkyl nitriles of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of functional products, e.g., garbage bags and the like.

THE INVENTION

The invention provides dimethyl substituted alkyl nitriles of our invention defined according to the generic structure:

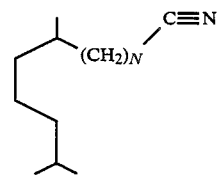

wherein N represents 0 or 1.

The dimethyl substituted alkyl nitriles of our invention produced according to the process of our invention are capable of augmenting or enhancing orris-like, cinnamon-like, sweet, citrus, lemony, fatty, coconut-like, rhodinol-like, minty, geranium-like and scorched linen aromas with floral undertones in perfume compositions, colognes and perfumed articles including soaps, bleaches, nonionic, cationic, anionic and zwitterionic detergents, fabric softener articles and perfumed articles.

The present invention also relates to process intermediates for producing said dimethyl substituted alkyl nitriles of our invention which process intermediates are defined according to the generic structure:

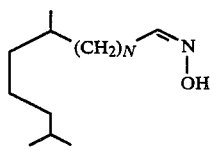

wherein N is 0 or 1

The dimethyl substituted alky nitriles of our invention are produced using as starting materials compounds defined according to the generic structure:

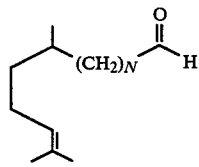

wherein N is 0 or 1.

These aldehydes are selectively hydrogenated whereby the carbon-carbon double bond moiety is reduced to a carbon-carbon single bond and the aldehyde moiety is retained intact thereby forming the group of compounds defined according to the structure:

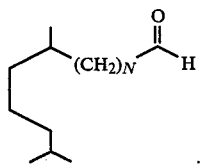

The compounds defined according to the structure:

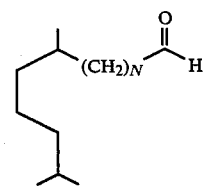

are then reacted with a hydroxyl amine salt defined according to the structure:

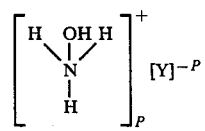

where Y represents an anion such as sulfate, chloride or bromide and P is 1 or 2 followed by reaction with base to form an aldoxime composition defined according to the structure:

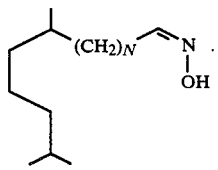

The resulting aldoxime having the structure:

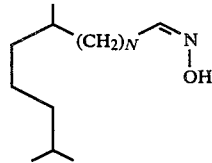

is then reacted with an appropriate conversion reagent to form the desired nitrile having the structure:

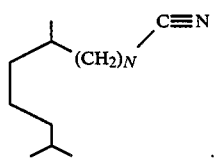

The resulting nitrile is then fractionally distilled from the reaction mass or otherwise separated in order to form the desired material useful in augmenting or enhancing the aroma of perfume compositions, colognes or perfumed articles.

In carrying out the reaction of the compounds defined according to the structure:

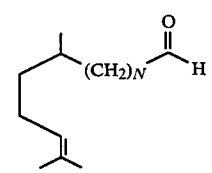

in order to form the compounds defined according to the structure:

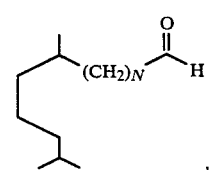

this reaction takes place at a temperature of from about 75° C. up to about 130° C. and a pressure of from about 100 up to about 1000 psig (pounds per square inch gauge) in the presence of a hydrogenation catalyst with hydrogen according to the reaction:

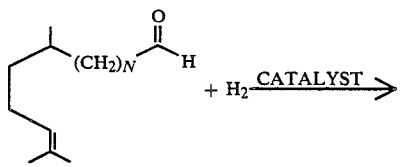

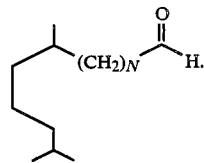

The hydrogenation catalyst must be such that it will selectively reduce the carbon-carbon double bond but not reduce the aldehyde moiety. Thus, we have found that the following palladium-containing catalysts are useful in the practice of this aspect of our invention:
(i) Palladium on calcium carbonate;
(ii) Palladium on carbon;
(iii) Palladium (II) acetate;
(iv) Palladium (II) acetylacetonate;
(v) Palladium (II) bromide;
(vi) Palladium (II) chloride;
(vii) Palladium hydroxide on carbon;
(viii) Palladium (II) iodide;
(ix) Palladium (II) nitrate hydrate;
(x) 1% Palladium on activated carbon;
(xi) 3% Palladium on activated carbon;
(xii) 5% Palladium on activated carbon;
(xiii) 10% Palladium on activated carbon;
(xiv) 1% Palladium on alumina;
(xv) 5% Palladium on alumina;
(xvi) 0.5% Palladium on alumina;
(xvii) 5% Palladium on barium carbonate;
(xviii) 5% Palladium on barium sulfate;
(xix) 5% Palladium on calcium carbonate;
(xx) 5% Palladium on calcium carbonate poisoned with lead (Lindar catalyst);
(xxi) 0.5% Palladium on 4 to 8-mesh carbon;
(xxii) 1% Palladium on 4 to 8-mesh carbon;
(xxiii) 5% Palladium sulfide on carbon;
(xxiv) Palladium (II) oxide;
(xxv) Palladium (II) oxide hydrate;
(xxvi) 20-40 Mesh Palladium-poly(ethylenimine);
(xxvii) 40-200 Mesh Palladium-poly(ethylenimine);
(xxviii) Palladium (II) sulfate; and
(xxix) Palladium (II) trifluoroacetate.

In carrying out the reaction of the aldehydes defined according to the structure:

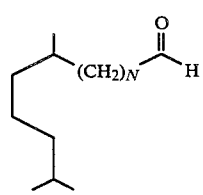

in order to form the aldoximes having the structure:

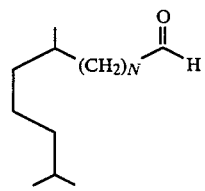

which reaction is set forth, thusly:

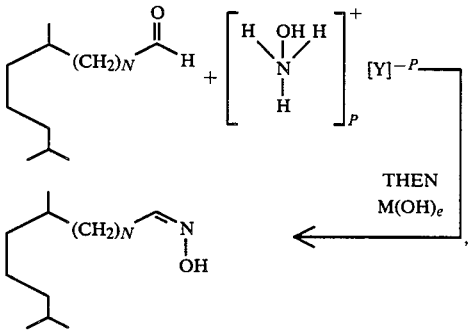

this reaction is carried out at 0°-40° C. at atmospheric pressure. The reaction is a two-stage reaction with the first stage being the reaction of the aldehyde having the structure:

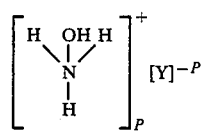

with the hydroxylamine salt having the structure:

$$\left[\begin{array}{c}H\phantom{OH}H\\ \diagdown\ |\ \diagup\\ N\\ |\\ H\end{array}\quad \begin{array}{c}OH\\ \end{array}\right]_P^+ [Y]^{-P}$$

(e.g., hydroxylamine hydrochloride or hydroxylamine sulfate). The second stage of the reaction is reaction with base with or without inert solvent. The base can be sodium hydroxide or calcium hydroxide (with e being 1 or 2).

In carrying out the dehydration of the aldoxime to form the nitrile the reaction is as follows:

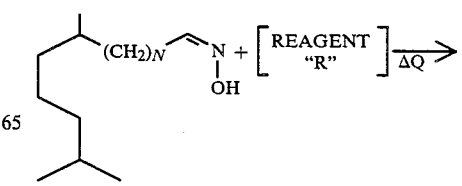

-continued

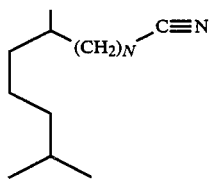

This reaction is carried out in refluxing inert solvent at a temperature in the range of from about 80° C. up to about 150° C. The dehydrating reagent "R" may be acetic anhydride, phosphorous trichloride, phosphorous oxychloride or thionylchloride. In place of acetic anhydride other organic anhydrides may be used such as propionic anhydride or mixed acetic-propionic anhydride defined according to the structure:

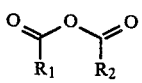

wherein $R_1$ and $R_2$ are the same or different methyl or ethyl.

Specific examples of the dimethyl substituted alkyl nitriles of our invention produced according to the foregoing process and useful for the practice of our invention are set forth in Table I below:

TABLE I

| Description of Composition With Structures: | Perfumery Evaluation |
| --- | --- |
| The compound having the structure:<br><br>prepared according to Example V, bulked distillation fractions 8-12. | An orris-like, cinnamon-like aroma profile with floral undertones. |
| The compound having the structure:<br><br>prepared according to Example V, distillation fraction 11. | A sweet, citrus (tart-lemon), cinnamic, fatty, lactonic (coconut) aroma profile. |
| The compound having the structure:<br><br>prepared according to Example II, bulked distillation fractions 8-20. | A rhodinal, minty, geranium-like profile. |
| The compound having the structure:<br><br>prepared according to Example III, bulked distillation fractions 5-. | A citrusy, fatty, scorched linen aroma profile. |

The dimethyl substituted alkyl nitriles of our invention and one or more auxiliary perfume ingredients, including, for example, hydrocarbons, alcohols, ketones, aldehydes, nitriles other than the nitriles of our invention, esters, lactones, ethers, synthetic essential oils and natural essential oils may be admixed so that the combined odors of the individual components produce a pleasant and desired fragrance, particularly and preferably in the citrusy and/or green, woody fragrances.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the overall sensory effect of the perfume composition will be at least the sum total of the effects of each of the ingredients. Thus, one or more of the dimethyl substituted alkyl nitriles of our invention can be used to alter, modify or enhance the aroma characteristics of a perfume composition, for example, by utilizing or moderating the olfactory reaction contributed by another ingredient in the composition.

The amount of one or more of the dimethyl substituted alkyl nitriles of our invention which will be effective in perfume compositions as well as in perfumed articles and colognes depends upon many factors, including the other ingredients, their amounts and the effects which are desired. It has been found that perfume compositions containing as little as 0.05% of one or more of the dimethyl substituted alkyl nitriles of our invention or even less (e.g., 0.02%) can be used to impart orris-like, cinnamon-like, sweet, citrus, lemony, fatty, coconut-like, rhodinol-like, minty, geranium-like and scorched linen aromas with floral undertones to soaps, cosmetics, detergents (including anionic, nonionic, zwitterionic and cationic solid or liquid detergents), bleach compositions or other products. The amount employed can range up to 70% of the fragrance components and will depend upon considerations of cost, nature of the end product, the effect desired on the finished product and the particular fragrance sought.

The dimethyl substituted alkyl nitriles of our invention are useful (taken alone or together with other ingredients in perfume compositions) in detergents and soaps, space odorants and deodorants, perfumes, colognes, toilet water, bath preparations such as lacquers, brilliantines, pomades and shampoos; cosmetic preparations, such as creams, deodorants, hand lotions and sun screens; powders such as talcs, dusting powders, face powders and the like. As little as 0.25% of one or more of the dimethyl substituted alkyl nitriles of our invention will suffice to impart an intense and substantive orris-like, cinnamon-like, sweet, citrus, lemony, fatty, coconut-like, rhodinol-like, minty, geranium-like and scorched linen aroma with floral undertones to citrusy and floral perfume formulations. Generally, no more than 5% of one or more of the dimethyl substituted alkyl nitriles of our invention based on the ultimate end product is required to be used "as-is" or in the perfume composition.

Furthermore, as little as 0.25% of one or more of the dimethyl substituted alkyl nitriles of our invention will suffice to impart such aroma to perfumed articles per se, whether in the presence of other perfume materials or whether used by itself. Thus, the range of use of one or more of the dimethyl substituted alkyl nitriles of our invention in perfumed articles may vary from about 0.25% up to about 5% by weight based on the total weight of the perfumed article.

In addition, the perfume composition or fragrance composition of our invention can contain a vehicle, or carrier for one or more of the dimethyl substituted alkyl nitriles of our invention. The vehicle can be a liquid such as a non-toxic alcohol, e.g., ethanol, a non-toxic glycol, e.g., propylene glycol or the like. The carrier can also be an absorbent solid, such as a gum (e.g., gum arabic), or components for encapsulating the composition by means of coacervation (such as gelatin).

It will thus be apparent that one or more of the dimethyl substituted alkyl nitriles of our invention can be utilized to alter, modify or enhance aromas of perfume compositions, colognes or perfumed articles.

Furthermore, several processes may be used in order to produce a thickened, highly viscous hypochlorite bleaching or sterilizing solution whereby the desired aroma profiles are imparted to the articles treated with said hypochlorite solutions.

Thus, for example, the dimethyl substituted alkyl nitriles of our invention may be premixed with the diphenyl oxide derivative or diphenyl oxide derivative-amine oxide solubilizer-stabilizer (having the structures, respectively:

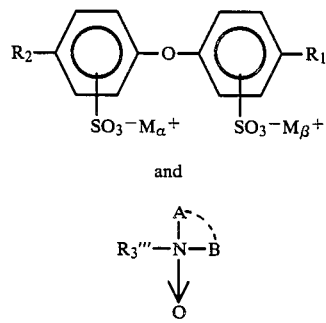

and the resulting dimethyl substituted alkyl nitrile-diphenyl oxide derivative or diphenyl oxide derivative-amine oxide premix is then mixed with the hypochlorite bleaching or sterilizing solution with stirring. Immediately after such addition, an aqueous alkali metal hydroxide solution is added to the mixture to bring the pH to the range of 11–14.0. A pH of less than 11 is not desired since it is difficult to achieve a single phase stable system at low pH's. A pH higher than 14.0 will also create a system which (1) is unnecessarily corrosive; (2) will narrow the range of perfume oils useable (in conjunction with one or more of the dimethyl substituted alkyl nitriles of our invention) of the system and (3) will limit the particular ingredients useable in such perfume oils in conjunction with one or more of the dimethyl substituted alkyl nitriles of our invention. On the other hand, if for example, one or more of the dimethyl substituted alkyl nitriles of our invention is used alone or further in combination with (i) diisoamylene epoxides; (ii) diisoamylenes as described in application for U.S. patent, Ser. No. 188,576 filed on Oct. 9, 1980 (now U.S. Pat. No. 4,303,555; or (iii) acyl diisoamylene derivatives as described in application for U.S. patent, Ser. No. 184,132 filed on Sept. 4, 1980 (now U.S. Pat. No. 4,321,255) and/or (iv) ketal derivatives of acyl diisoamylene derivatives described in application for U.S. patent, Ser. No. 212,993 filed on Dec. 4, 1980, (now U.S. Pat. No. 4,315,952) a pH of about 14.0 and even slightly higher (e.g., 14.1) is acceptable.

The aqueous alkali metal hydroxide can be added to the aqueous alkali metal hypochlorite solution before adding the diphenyl oxide derivatives (taken alone or in conjunction with the amine oxide) or the dimethyl substituted alkyl nitriles of our invention or mixture of dimethyl substituted alkyl nitriles of our invention with other materials such as diisoamylene epoxides. Indeed, the ingredients: the dimethyl substituted alkyl nitriles of our invention; the alkali metal hydroxide and the diphenyl oxide derivative or diphenyl oxide derivative-amine oxide composition (having the structures, respectively:

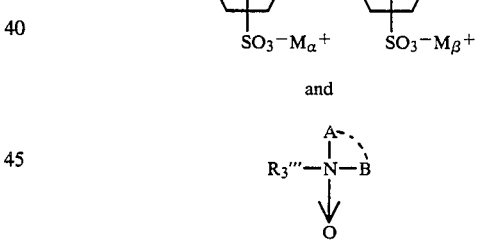

may be added or admixed in any order which is convenient to the formulator.

The alkali metal hypochlorites preferred in the practice of our invention are: sodium hypochlorite, potassium hypochlorite and lithium hypochlorite or mixtures of same. The alkali metal hypochlorites preferred in the practice of this invention are: lithium hydroxide, potassium hydroxide and sodium hydroxide, or, if desired, mixtures of such hydroxides.

The temperature at which the composition of our invention remains both substantially stable and commercially useful for the purposes set forth herein (that is, remains as clear single aqueous or gel phase) and retains (1) the desired properties inherent in the known bleaching and sterilizing uses of aqueous alkali metal hypochlorite liquid or gel solutions, and (2) the properties imparted thereto as a result of the use of one or more of the dimethyl substituted alkyl nitriles of our invention which impart to articles previously subjected to the aqueous alkali metal hypochlorite gel or liquid solutions a desired aroma profile, varies from approximately 20° F. up to approximately 120° F. At temperatures below 20° F. a two-phase system usually occurs and at temperatures higher than 120° F. the bleaching or sterilizing efficiency of the compositions of our invention is diminished at an excessive rate.

When it is desired to (1) initially form the $C_{10}$–$C_{12}$ straight chain or branched chain diphenyl oxide alkali metal sulfonate or diphenyl oxide derivative-amine oxide-dimethyl substituted alkyl nitrile premix; (2) then combine the resulting premix with an alkali metal hypochlorite solution; (3) then add the thickening agent and then (4) adjust the pH of the resulting solution to the range of 11–14.0, then the temperature of mixing ranges which are considered to be within the scope of this invention are as follows:
(a) Formation of the diphenyl oxide derivative or diphenyl oxide-amine oxide-dimethyl substituted alkyl nitrile premix 20° F.–150° F.
(b) Mixing the premix with aqueous alkali metal hypochlorite solution followed by thickening agent 20° F.–120° F.
(c) Adjustment of the pH of the solution to the range of 11–14.0 using aqueous alkali metal hydroxide solution 20° F.–120° F.

In any event, whenever a mixing unit operation involves the aqueous alkali metal hypochlorite solution, the temperature of mixing is limited to the range of 20° F.–120° F. Where the mixing unit operation involves the mixing of one or more of the dimethyl substituted alkyl nitriles of our invention, the upper bound of the temperature range is limited by the stability of the specific dimethyl substituted alkyl nitriles of our invention or other perfume ingredient mixed with the dimethyl substituted alkyl nitriles of our invention useable in the practice of our invention; and the lower bound of said temperature range is limited by the least temperature where a single liquid phase or gel phase including one or more of the dimethyl substituted alkyl nitriles of our invention or other ingredients admixed therewith will exist. Where a unit mixing operation of the process of our invention involves the mixing of one or more diphenyl oxide derivatives having the generic structure:

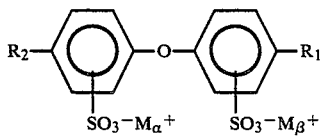

taken alone or taken together with one or more amine oxides having the generic structure:

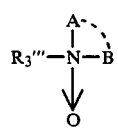

with other materials, the upper bound of the temperature range is the decomposition point of any one of the diphenyl oxide derivatives or amine oxide components and the lower bound is the least temperature where a single liquid phase or gel phase, including the diphenyl oxide derivatives or diphenyl oxide-amine oxide mixture will exist.

Preferred diphenyl oxide derivative compositions from a practical standpoint useful in the practice of our invention are compounds having the structure:

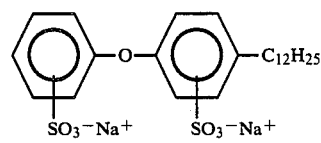

where the $C_{12}H_{25}$ moiety represents one or a series of different branched chains; compounds defined according to the structure:

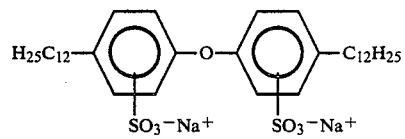

where the $C_{12}H_{25}$ moiety represents one or a series of different branched chains; compounds defined according to the structure:

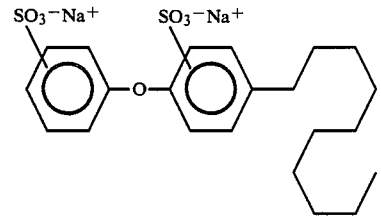

and compounds defined according to the structure:

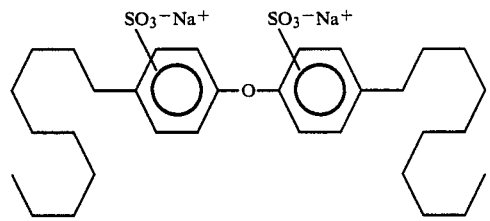

otherwise known as DOWFAX®2A1 in the case where one or $R_1$ or $R_2$ represents branched $C_{12}H_{25}$ alkyl chains and the other of $R_1$ or $R_2$ represents hydrogen, or DOWFAX®3B2 in the case where one one of $R_1$ or $R_2$ represents straight $C_{10}$ alkyl chain and the other of $R_1$ or $R_2$ represents hydrogen (DOWFAX® being a registered trademark of the Dow Chemical Company of Midland, Mich.).

When used in conjunction with the diphenyl oxide derivatives preferred amine oxide compositions, from a practical standpoint, useful in the practice of our invention are the commercially available (1) dimethyl "cocoamine" oxide (a mixture which is dominated by dimethyl-$C_{12}$–$C_{16}$ straight chain alkyl amine oxides; more particularly a mixture containing approximately 70% $C_{12}$ straight chain alkyl amine oxides, approximately 25% of straight chain $C_{14}$ alkyl amine oxides and approximately 4% straight chain $C_{16}$ alkyl amine oxides) and (2) N-cocomorpholine oxide, a mixture dominated by straight chain $C_{12}$–$C_{16}$ alkyl morpholine oxides (specifically containing approximately 70% straight chain $C_{12}$ alkyl morpholine oxide, approximately 25% straight chain $C_{14}$ alkyl morpholine oxide, and approximately 4% straight chain $C_{16}$ alkyl morpholine oxide). Commercial examples of such amine oxide compositions are: AROMOX® DMC-W and AROMOX® DMMC-W which are 30% aqueous dimethyl cocoamine oxide solutions and AROMOX® NCMDW which is a 40% aqueous N-cocomorpholine oxide solution each of which is produced by the Armac Division of AKZO of Chicago, Ill. These materials are described in Brochure 68011, published by Armour Industrial Chemicals, P.O. Box 1805, Chicago, Ill. 60690. Other preferred amine oxides are n-undecyl dimethyl amine oxide and n-tridecyl dimethyl amine oxide.

The percentage of hypochlorite ion in the compositions of our invention may vary from about 1% up to about 20% for the desired effects to be produced using the diphenyl oxide derivative or diphenyl oxide derivative amine oxide-dimethyl substituted alkyl nitrile covered by our invention. The usual percent of alkali metal hypochlorite in solution is about 5%, the percentage of sodium hypochlorite in such mixtures as CLOROX® the registered trademark of the Clorox Corporation.

The perfume oil used in conjunction with one or more of the dimethyl substituted alkyl nitriles of our invention which, in turn, is used in conjunction with the aqueous alkali metal hypochlorite solution must have such properties as to be able (1) to be compatible with one or more of the dimethyl substituted alkyl nitriles of our invention; (2) to impart to the resulting or "aqueous alkali metal hypochlorite" liquid or gel solution a pleasant aroma which harmonizes with the aroma of one or more of the dimethyl substituted alkyl nitriles of our invention; (3) to effect a substantial diminution or elimination of the disagreeable "hypochlorite" aroma which is imparted to the surfaces (e.g., bleached laundry or the hands of the user which are in direct contact with the hypochlorite solution) on which known aqueous alkali metal hypochlorite solutions have been used; and (4) to impart to the surfaces with which such aqueous alkali metal hypochlorite solutions are in contact, a pleasant long lasting stable aroma.

The term "compatible" is herein intended to mean two situations:

(a) a first situation where the perfume component has no destructive effect upon the alkali metal hypochlorite compound whereby the alkali metal hypochlorite will be oxidized or reduced; and
(b) the alkali metal hypochlorite has no effect upon the perfume oil or any of the perfume oil components including one or more of the dimethyl substituted alkyl nitriles of our invention whereby such perfume oil or perfume oil component will be oxidized or reduced as a result of contact with the hypochlorite solution.

Examples of ingredients compatible with one or more of the dimethyl substituted alkyl nitriles of our invention and suitable for the aforementioned purposes, that is, useable in conjunction with the hypochlorites, amine oxide derivatives and diphenyl oxide derivatives of our invention are as follows:

1. Cedryl alkyl ethers covered by U.S. Pat. No. 3,373,208 such as cedryl methyl ether;
2. Isochroman musks covered by U.S. Pat. No. 3,360,530 and 3,591,528 such as 6-oxa-1.1,3,3,8-pentamethyl-2,3,5,6,7,8-hexahydro-1H-benz(f)indene;
3. Polycyclic ethers covered by U.S. Pat. No. 3,281,432, such as octahydro-1,3a,6-trimethyl-1H-1,6a,ethanopentaleno-(1,2-C)furan;
4. Polycyclic ketones such as hexahydro-1,1,5,5-tetramethyl-2H-2,4a-methanonaphthalen-8-(5H)one;
5. Diisoamylenes described according to application for U.S. patent, Ser. No. 188,576 filed on Sept. 18, 1980 (now U.S. Pat. No. 4,303,555);
6. Acyl diisoamylene derivatives described according to application for U.S. patent, Ser. No. 184,132 filed on Sept. 4, 1980 (now U.S. Pat. No. 4,321,255) and ketal derivatives thereof described according to application for U.S. patent, Ser. No. 212,993 filed on Dec. 4, 1980 (now U.S. Pat. No. 4,315,952);
7. Diisoamylene epoxide derivatives prepared according to application for U.S. patent, Ser. No. 231,773 filed on Feb. 27, 1981 (now U.S. Pat. No. 4,330,425);
8. 2-Methyl-2-octanol used in accordance with the disclosure of U.S. Pat. No. 4,390,448 issued on June 28, 1983 the specification for which is incorporated herein by reference; and
9. Ethyl norbornylalkyl ethers described according to application for U.S. patent, Ser. No. 149,676 filed on Jan. 28, 1988.

It will be understood that a number of materials which add to the orris-like, cinnamon-like, sweet, citrusy, lemony, fatty, coconut-like, rhodinol-like, minty, geranium-like and scorched linen-like aromas (with floral undertones) of the dimethyl substituted alkyl nitriles of our invention additional nuances, e.g., eucalyptol-like or minty or woody nuances, will not be useful for our invention because they are, interalia, easily oxidized by the alkali metal hypochlorite in the system. Examples are 1,5,9-trimethyl-12-acetyl-cyclododecatriene-1,5,8 and 1,5,9-trimethyl-12-cyclododecadiene-1,8 covered by British Pat. No. 1,204,409.

A basic feature of our invention concerns the fact that the only detergent group needed or desirable in the composition of our invention is the class of diphenyl oxide derivatives defined according to the structure:

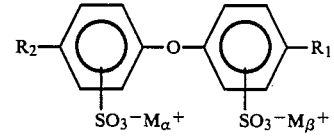

wherein $R_1$, $R_2$, $M_\alpha$ and $M_\beta$ are defined, supra, taken alone or in conjunction with the class of morpholino and/or dimethyl $C_{11}$-$C_{13}$ straight chain alkyl amine oxides defined according to the structure:

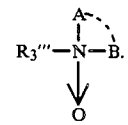

More specifically, such detergents as sodium decyl ether sulfate, sodium myristyl ether sulfate, sodium lauryl ether sulfate and lithium lauryl ether sulfate are neither desired nor are they required. Furthermore, the well known hydrotropes employed in prior art compositions such as the well known family of clarifying agents comprising the alkali metal or alkali earth metal salts of mono- and polyalkylated benzene or naphthalene sulfonates such as sodium xylene or magnesium toluene sulfonate are again neither desired nor are they required in the compositions intended to be encompassed by the instant invention.

Another basic feature of our invention concerns the fact that when it is desired to have a gel phase composition, thickener agents may be employed in conjunction with the system; hypochlorite bleach-dimethyl substituted alkyl nitrile-diphenyl oxide derivative or diphenyl oxide derivative-amine oxide derivative (having the general structure:

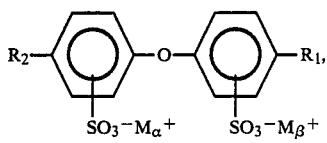

and having the structure:

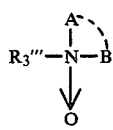

of our invention.

Still another basic feature of our invention concerns the fact that the gel phase composition including thickener agents are employed with the "premix" system: dimethyl substituted alkyl nitrile-diphenyl oxide derivative or diphenyl oxide derivative-amine oxide of our invention.

Thus, sodium palmitate, sodium stearate, sodium laurate, potassium palmitate, potassium stearate, potassium laurate, lithium palmitate, lithium stearate and/or lithium laurate or combinations of the foregoing may be added to the compositions of matter of our invention to provide a thickened gel-type hypochlorite bleach which is, in addition to being in a semi-solid state, is unobviously, advantageously and unexpectedly stable over long periods of time. Percentages of thickening agents such as sodium palmitate, sodium stearate, sodium laurate, potassium palmitate, potassium stearate, potassium laurate, lithium palmitate, lithium stearate or lithium laurate or combinations of these which may be used in the thickened compositions of our invention are from 1% by weight up to 12% by weight of the thickener based on the overall weight of the hypochlorite bleach-diphenyl oxide derivative (or diphenyl oxide derivative-amine oxide)dimethyl substituted alkyl nitrile composition of our invention. When it is merely desired to have a thickened "premix" the percentage of thickening agent may vary from about 5% up to about 40% by weight of thickener based on overall weight of "premix".

The following Examples I-V serve to illustrate processes for producing the dimethyl substituted alkyl nitriles useful in our invention. Examples following Example V in general serve to illustrate organoleptic utilities of the dimethyl substituted alkyl nitriles of our invention.

In general, the following examples serve to illustrate specific embodiments of our invention. It will be understood that these examples are illustrative and that the invention is to be considered restricted thereto only as indicated in the appended claims. All parts and percentages given herewith are by weight unless otherwise specified.

EXAMPLE I

Hydrogenation of Eucalyptus Citriodora

Reaction:

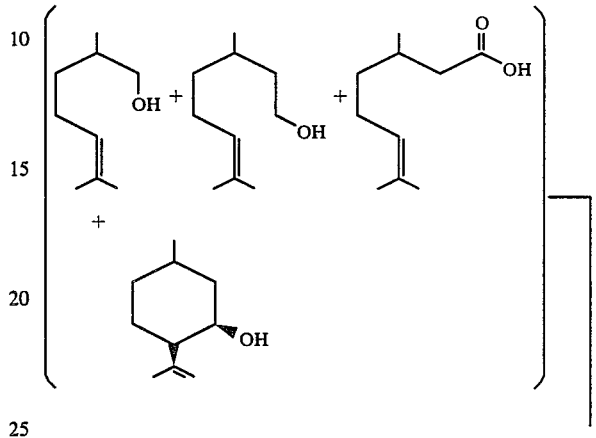

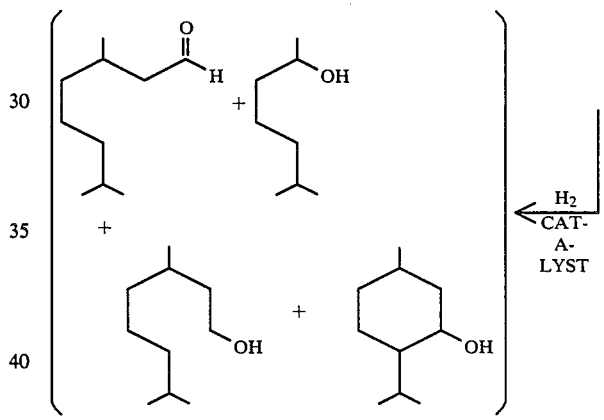

Into a 2 liter autoclave is placed the following ingredients:

| | |
|---|---|
| Eucalyptus citriodora | 1175 grams |
| 5% Palladium on carbon catalyst (Hereaus V-0203) | 12 grams |
| Calcium carbonate | 6 grams |

The autoclave is sealed and pressurized to 300 psig with hydrogen, while maintained at a temperature of a 100°-105° C.

When 630 psig of hydrogen has been taken up, the reaction slows down considerably. At this point in time 12% starting materials still remains.

150 Grams of isopropyl alcohol and 0.5% (6 grams) of catalyst is then added to the autoclave and the autoclave is again resealed and repressurized. An additional 170 psig of hydrogen uptake occurred. Analysis indicates that the reaction has now gone to completion.

FIG. 1 is the GLC profile for the resulting reaction product. (Conditions: Bonded methyl silicone column (OV-1) programmed at 80°-220° C. at 2° C. per minute).

The peak indicated by reference numeral 10 is the peak for the isopropyl alcohol solvent.

The peak indicated by reference numeral 12 is the peak for the saturated aldehyde having the structure:
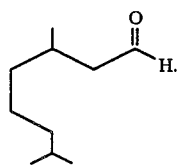
EXAMPLE II
Preparation of 3,7-Dimethyl octano nitrile
Reactions:
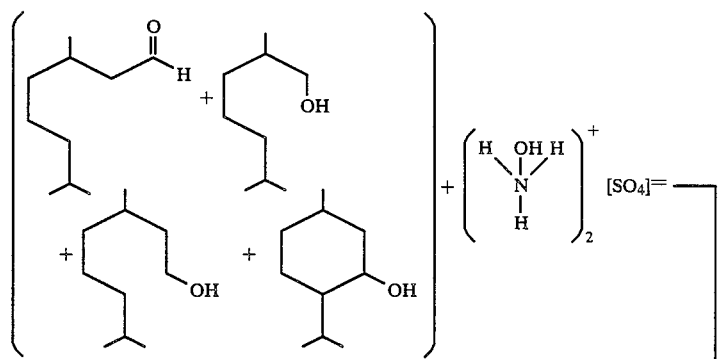
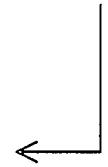
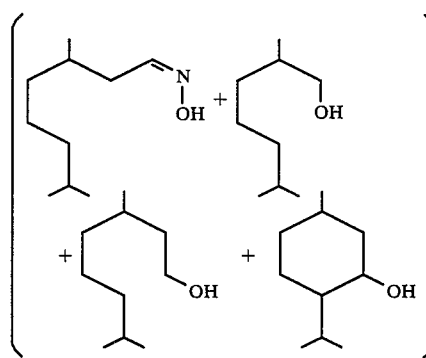
and
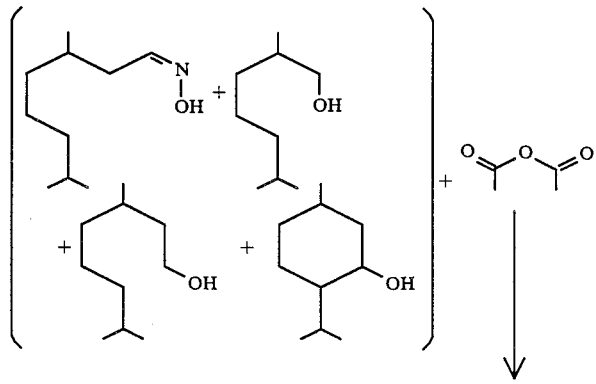

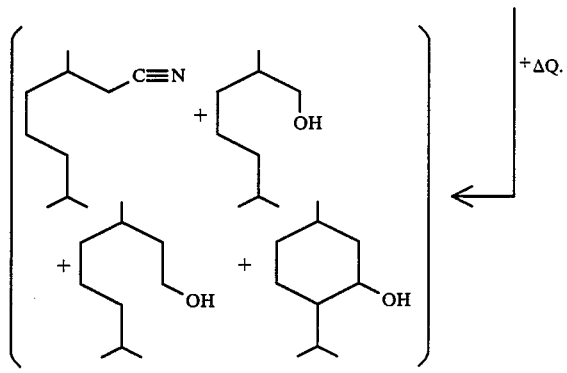

Into a 5 liter reaction vessel equipped with stirrer, thermometer, heating mantle and reflux condenser, are placed one liter water, 393 grams of hydroxylamine hydrogen sulfate having the formula:

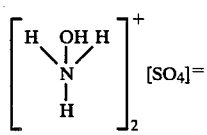

and 900 grams of the reaction product of Example I containing compounds having the structures:

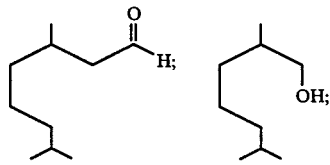

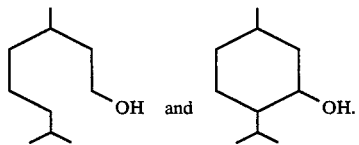

The reaction mass is stirred for a period of 15 minutes at 20° C.

Over a period of two hours, 416 grams of 50% aqueous sodium hydroxide is added to the reaction mass.

The reaction mass is aged for one hour and 400 ml toluene is added. The resulting organic phase is separated from the aqueous phase. The organic phase is washed with 1 liter 5% aqueous sodium chloride.

The resulting crude oxime reaction product (1983.5 grams) containing the compound having the structure:

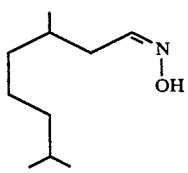

is then retained for further reaction.

Into a 5 liter reaction vessel equipped with stirrer, thermometer, reflux condenser and heating mantle is placed 551 grams of acetic anhydride. The acetic anhydride is heated to 80° C. and over a period of two hours, the crude oxime reaction product containing the compound having the structure:

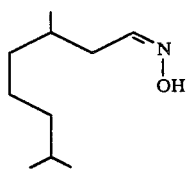

is added to the acetic anhydride while maintaining the reaction mass at 80° C. with stirring. The reaction mass is then aged for 0.5 hours at 80° C.

The reaction mass is then quenched with 1.5 liters of water and the organic phase is separated from the aqueous phase. The organic phase is then saponified with 250 grams of 50% aqueous sodium hydroxide, 250 ml water and 200 ml methyl alcohol.

The resulting product is then fractionally distilled yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 23/24 | 23/60 | 100/70 | 100% | 314.6 |
| 2 | 50 | 70 | 70 | 100% | 347.7 |
| 3 | 40 | 105 | 17 | 100% | 248.7 |
| 4 | 85 | 96 | 8 | 9:1 | 39.0 |
| 5 | 83 | 90 | 6 | 9:1 | 34.8 |
| 6 | 83 | 92 | 6 | 9:1 | 31.4 |
| 7 | 93 | 90 | 6 | 9:1 | 35.2 |
| 8 | 83 | 90 | 5 | 9:1 | 39.2 |
| 9 | 83 | 90 | 5 | 9:1 | 31.3 |
| 10 | 83 | 90 | 5 | 3:1 | 42.7 |
| 11 | 83 | 92 | 4 | 3:1 | 27.8 |
| 12 | 83 | 92 | 4 | 3:1 | 25.4 |
| 13 | 83 | 92 | 4 | 3:1 | 32.6 |
| 14 | 83 | 92 | 4 | 3:1 | 36.7 |
| 15 | 90 | 93 | 4.5 | 3:1 | 46.3 |
| 16 | 90 | 93 | 4.5 | 3:1 | 43.2 |
| 17 | 90 | 94 | 4.5 | 3:1 | 37.3 |
| 18 | 90 | 95 | 4.5 | 3:1 | 42.5 |
| 19 | 90 | 96 | 4.5 | 3:1 | 32.4 |
| 20 | 90 | 100 | 4.5 | 3:1 | 42.7 |
| 21 | 90 | 110 | 4.5 | 3:1 | 30.3 |
| 22 | 90 | 147 | 4.5 | 3:1 | 27.9 |
| 23 | 90 | 165 | 4.5 | 3:1 | 19.8. |

Fractions 8–20 are bulked. The bulked fractions have a rhodinol-like, minty and geranium-like aroma profile.

FIG. 2 is the GLC profile for the crude reaction product. The peak indicated by reference numeral 21 is the peak for toluene. The peak indicated by reference numeral 22 is the peak for the compound having the structure:

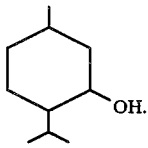

The peak indicated by reference numeral 23 is the peak for the compound having the structure:

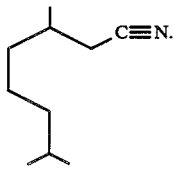

EXAMPLE III

Preparation of 3,8-Dimethyl Octyl Nitrile

Reactions:

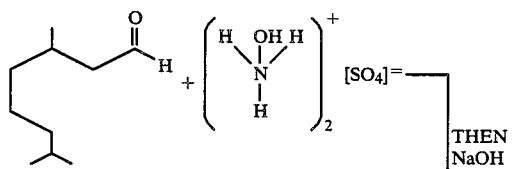

and

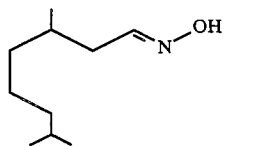

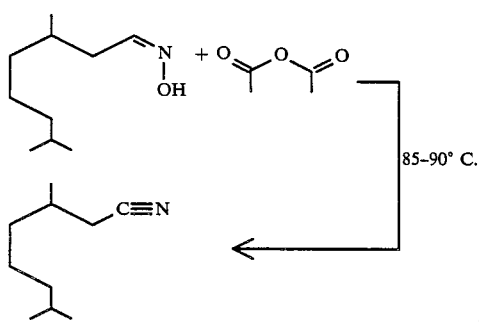

Into a 5 liter reaction vessel equipped with stirrer, thermometer, cooling coils and heating mantle are placed 2282 grams of water and 580 grams of hydroxylamine sulfate having the structure:

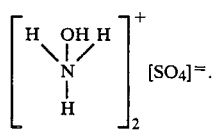

The resulting mixture is cooled to 10° C. Over a period of ten minutes, 1000 grams of 3,8-dimethyloctanal having the structure:

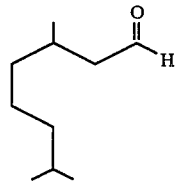

is added to the reaction mass.

Over a period of one hour, 604 grams of 50% aqueous sodium hydroxide is added to the reaction mass while maintaining the temperature of the reaction mass at 10°-15° C. The reaction mass is then aged for an additional three hours at 10°-15° C.

At the end of the three hour aging period, 630 ml toluene is then added to the reaction mass. The reaction mass is then quenched into water and the organic phase is separated from the aqueous phase. The organic phase is washed with a 5% aqueous sodium chloride solution.

The resulting crude reaction product is then retained for the subsequent reaction.

Into a 5 liter reaction vessel equipped with stirrer, thermometer, heating mantle and reflux condenser is placed 1157 grams of acetic anhydride. The acetic anhydride composition is heated to 85° C. and over a period of one hour to oxime reaction product produced, supra, containing the compound having the structure:

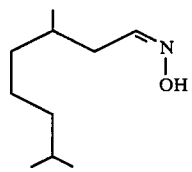

is fed into the acetic anhydride at a temperature in the range of from 85° C. up to 90° C. The resulting reaction mass is aged with stirring for a period of one hour at 90° C.

The resulting reaction mass is then cooled to 80° C. and one liter of water is added. The organic phase is separated from the aqueous phase and the organic phase is washed with a 5% aqueous sodium bicarbonate solution.

The resulting organic phase is then fractionally distilled yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 23/35 | 23/110 | 150/10 | 100% | 221.7 |
| 2 | 72 | 85 | 3.0 | 9:1 | 38.1 |
| 3 | 72 | 85 | 5.0 | 9:1 | 34.9 |
| 4 | 68 | 80 | 3.0 | 9:1 | 27.1 |
| 5 | 68 | 80 | 3.0 | 9:1 | 36.5 |

-continued

| Fraction No. | Vapor Temp. (°C.) | Liquid Temp. (°C.) | Vacuum mm/Hg. Pressure | Reflux Ratio | Weight of Fraction |
|---|---|---|---|---|---|
| 6 | 68 | 80 | 3.0 | 9:1 | 24.2 |
| 7 | 68 | 80 | 3.0 | 9:1 | 42.0 |
| 8 | 68 | 80 | 3.0 | 9:1 | 46.0 |
| 9 | 68 | 80 | 3.0 | 4:1 | 27.9 |
| 10 | 62 | 82 | 3.0 | 4:1 | 41.9 |
| 11 | 62 | 82 | 3.0 | 4:1 | 32.5 |
| 12 | 62 | 82 | 3.0 | 4:1 | 41.2 |
| 13 | 62 | 85 | 3.0 | 4:1 | 30.5 |
| 14 | 62 | 87 | 2.5 | 4:1 | 34.7 |
| 15 | 62 | 93 | 2.4 | | 35.7 |
| 16 | 62 | 105 | 2.4 | | 28.9 |
| 17 | 63 | 135 | 2.6 | | 24.5 |
| 18 | 60 | 180 | 2.5 | | 20.3. |

FIG. 3 is the GLC profile for the crude reaction product prior to distillation. The peak indicated by reference numeral 31 is the peak for the solvent. The peak indicated by reference numeral 33 is the peak for the desired nitrile product having the structure:

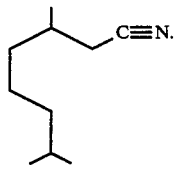

FIG. 4 is the GLC profile for the oxime intermediate reaction product. The peak indicated by reference numeral 41 is the peak for the desired nitrile having the structure:

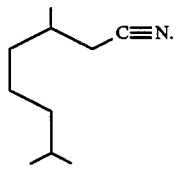

The peaks indicated by reference numerals 42 and 43 are for the oxime intermediate having the structure:

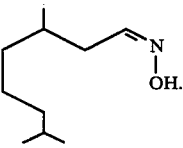

FIG. 5 is the NMR spectrum for the compound having the structure:

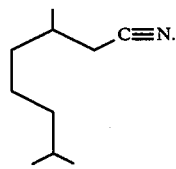

The foregoing distillation fractions 5–15 are bulked. Bulked distillation fractions 5–15 have a citrusy, fatty, scorched linen aroma profile.

EXAMPLE IV

Preparation of 2,6-Dimethyl Heptanal

Reaction:

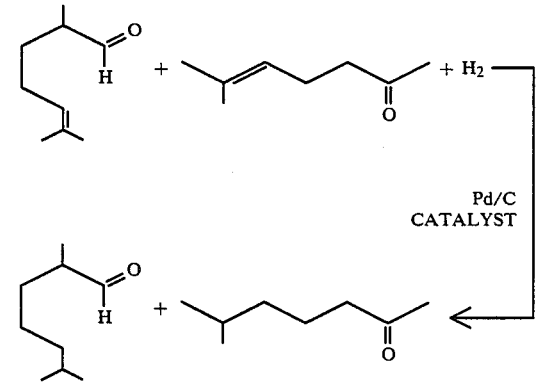

Into a 1 liter autoclave equipped with hydrogen feed is placed 500 grams of melonal (commercial) consisting of the compounds having the structures:

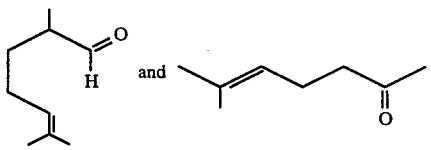

and 7.5 grams of 5% palladium on carbon (catalyst).

The autoclave is sealed and hydrogen is fed into the autoclave keeping the pressure at 300 psig and the temperature at 75°–123° C. The hydrogenation is carried out for a period of five hours (uptake of hydrogen: 3.57 moles or 1017 psig).

The autoclave is cooled at the end of the five hour period and opened. The resulting product having the structures:

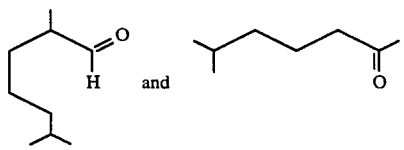

is then fractionally distilled.

FIG. 6 is the NMR spectrum for the compound having the structure:

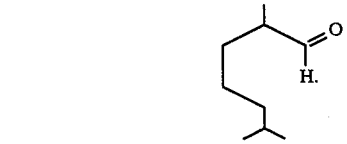

EXAMPLE V

Preparation of 2,5-Dimethylheptane Nitrile

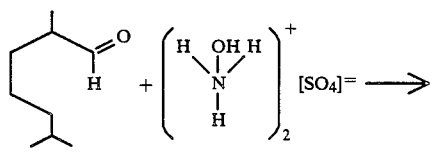

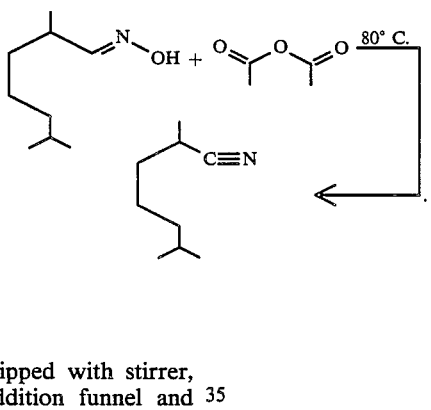

Into a 3 liter reaction flask equipped with stirrer, thermometer, reflux condenser, addition funnel and cooling bath is placed 198 grams of hydroxylamine sulfate having the structure:

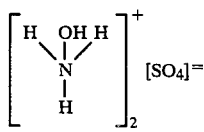

dissolved in 500 ml water. The reaction mass is cooled to 15° C. and 450 grams of the aldehyde having the structure:

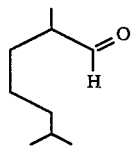

prepared according to Example IV is added to the reaction mass.

Over a period of 45 minutes, 298 grams of 50% aqueous sodium hydroxide is added to the reaction mass while keeping the temperature thereof at 15°–25° C.

While maintaining the reaction mass at a temperature of 25° C., 310 ml toluene is added thereto.

The resulting organic phase is separated from the aqueous phase and the organic phase is washed with 800 ml 5% aqueous sodium chloride.

The resulting organic phase contains the oxime having the structure:

Into the 3 liter reaction flask equipped with stirrer, thermometer, reflux condenser, addition funnel and cooling bath is placed 471 grams of acetic anhydride. The acetic anhydride is heated to 80° C. and over a period of two hours, the oxime having the structure:

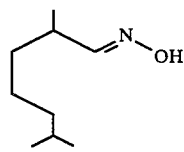

is added to the acetic anhydride while maintaining the temperature of the reaction mass at 80° C. The resulting reaction mass is then aged with stirring for a period of two hours and then washed with 5% aqueous sodium carbonate and distilled on a 12" Goodloe column yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 38/45 | 60/75 | 50/10.0 | 9:1 | 15.0 |
| 2 | 62 | 90 | 20 | 9:1 | 6.0 |
| 3 | 60 | 95 | 20 | 9:1 | 8.0 |
| 4 | 85 | 95 | 20 | 9:1 | 11.0 |
| 5 | 90 | 100 | 30 | 9:1 | 6.0 |
| 6 | 89 | 100 | 30 | 9:1 | 7.0 |
| 7 | 88 | 99 | 28 | 9:1 | 6.0 |
| 8 | 87 | 95 | 25 | 9:1 | 6.0 |
| 9 | 88 | 100 | 25 | 9:1 | 7.0 |
| 10 | 85 | 104 | 25 | 9:1 | 7.0 |

-continued

| Fraction No. | Vapor Temp. (°C.) | Liquid Temp. (°C.) | Vacuum mm/Hg. Pressure | Reflux Ratio | Weight of Fraction |
|---|---|---|---|---|---|
| 11 | 80 | 107 | 20 | 9:1 | 8.0 |
| 12 | 80 | 125 | 20 | 9:1 | 8.0 |
| 13 | 75 | 135 | 19 | 9:1 | 7.0 |
| 14 | 60 | 139 | 19 | 9:1 | 7.0 |
| 15 | 50 | 165 | 20 | 9:1 | 5.0 |
| 16 | 50 | 175 | 20 | 9:1 | 2.0 |

FIG. 7 is the GLC profile for the oxime intermediate reaction product prior to reaction with acetic anhydride. The peack indicated by reference numeral 71 is the peak for the compound having the structure:

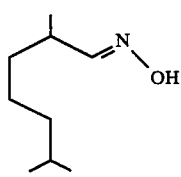

(Conditions: SE-30 column programmed at 180C isothermal).

FIG. 8 is the GLC profile for the nitrile reaction product. The peak indicated by reference numeral 81 is the peak for the compound having the structure:

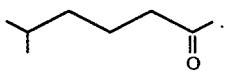

The peak indicated by reference numeral 82 is the peak for the nitrile having the structure:

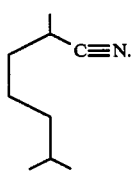

FIG. 9 is the NMR spectrum for the compound having the structure:

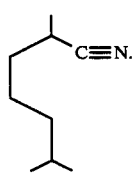

The resulting product (bulked distillation fractions 8-12) containing essentially the compound having the structure:

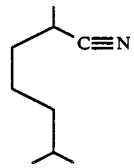

has an orris-like, cinnamon-like aroma profile with floral undertones.

Nitriles defined according to the generic structure:

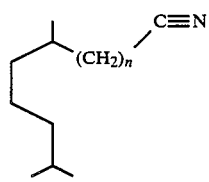

may be prepared using methods other than those set forth in the foregoing Examples I-V. Thus, for example, the corresponding alcohols may be reacted with ammonia and hydrogen in the presence of a catalyst at a temperature of 260°-340° C. according to the reaction:

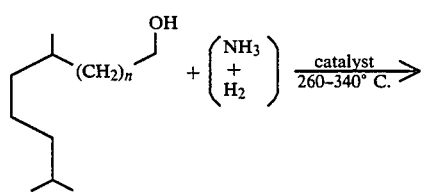

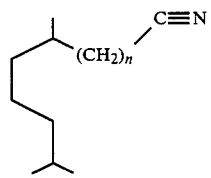

according to U.S. Pat. No. 4,731,464 issued on Mar. 15, 1988 the specification for which is incorporated by reference herein.

Furthermore, another method of reaction is to react the corresponding halide with an alkali metal cyanide according to the reaction:

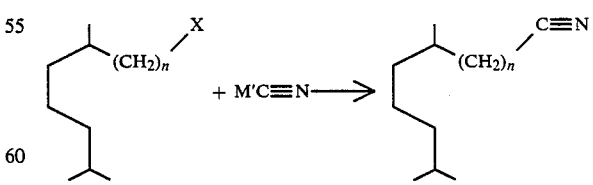

wherein X represents a halogen such as chloro, bromo or iodo; N is 0 or 1; and M' represents alkali metal, e.g., sodium, lithium or potassium.

EXAMPLE VI

The following Chypre formuations are prepared:

| Ingredients | Parts by Weight | | | |
|---|---|---|---|---|
| | VI(A) | VI(B) | VI(C) | VI(D) |
| Musk ambrette | 40 | 40 | 40 | 40 |
| Musk ketone | 60 | 60 | 60 | 60 |
| Coumarin | 30 | 30 | 30 | 30 |
| Oil of bergamot | 150 | 150 | 150 | 150 |
| Oil of lemon | 100 | 100 | 100 | 100 |
| Methyl ionone | 50 | 50 | 50 | 50 |
| Hexyl cinnamic aldehyde | 100 | 100 | 100 | 100 |
| Hydroxycitronellal | 100 | 100 | 100 | 100 |
| Oil of lavender | 50 | 50 | 50 | 50 |
| Texas cedarwood oil | 85 | 85 | 85 | 85 |
| Virginia cedarwood oil | 30 | 30 | 30 | 30 |
| Oil of sandalwod (East Indies) | 40 | 40 | 40 | 40 |
| Isoeugenol | 20 | 20 | 20 | 20 |
| Eugenol | 10 | 10 | 10 | 10 |
| Benzyl acetate | 30 | 30 | 30 | 30 |
| β-phenyl ethyl alcohol | 40 | 40 | 40 | 40 |
| α-phenyl ethyl alcohol | 30 | 30 | 30 | 30 |
| Oakmoss absolute | 30 | 30 | 30 | 30 |
| Vetiver oil Venezuela | 25 | 25 | 25 | 25 |
| The compound having the structure: 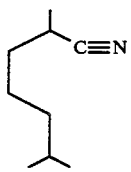 prepared according to Example V, bulked distillation fractions 8-12. | 62 | 0 | 0 | 31 |
| Compound having the structure: 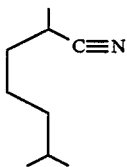 prepared according to Example V, distillation fraction 11. | 0 | 62 | 0 | 0 |
| Compound having the structure: 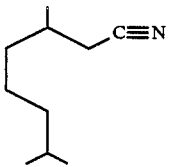 prepared according to Example II, bulked fractions 8-20. | 0 | 0 | 62 | 0 |
| The compound having the structure: 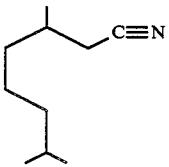 prepared according to Example III, bulked fractions 5-15. | 0 | 0 | 0 | 31 |

The compound having the structure:

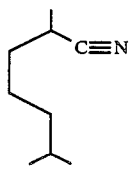

prepared according to Example V, bulked fractions 8-12 imparts to this Chypre formulation an intense orris-like, cinnamon-like topnote and a floral undertone. Accordingly, the formulation of Example VI(A) can be described as "Chypre having orris-like and cinnamon-like topnotes and floral undertones".

The compound having the structure:

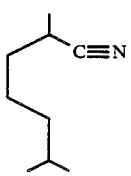

prepared according to Example V, fraction 11 imparts to this Chypre formulation an intense and long-lasting, sweet, citrus (tart-lemon), cinnamon, fatty, lactonic (coconut) undertone. Accordingly, the formulation of Example VI(B) can be described as "Chypre having a sweet, citrus (tart-lemon), cinnamon-like, fatty, coconut-like undertone".

The compound having the structure:

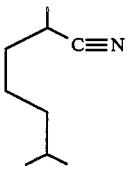

prepared according to Example II (bulked fractions 8-20) imparts to this Chypre formulation an intense and long-lasting rhodinol-like, minty and geranium-like undertone. Accordingly, the formulation of Example VI(C) can be described as "Chypre having rhodinol-like, minty and geranium-like undertones".

The mixture of compounds having the structures:

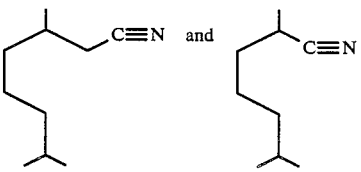

prepared according to Example III (bulked fractions 5-15) and Example V (bulked fractions 8-12) imparts to this Chypre formulation orris-like and cinnamon-like topnotes with floral, citrusy, fatty and scorched linen undertones. Accordingly, the formulation of Example VI(D) can be described as "Chypre having orris-like and cinnamon-like topnotes and floral, citrusy, fatty and scorched linen undertones.

EXAMPLE VII

Preparation of Cosmetic Powder Compositions

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
| --- | --- |
| Compound having the structure: 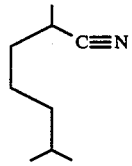 prepared according to Example V, bulked distillation fractions 8-12 | An orris-like and cinnamon-like aroma profile with floral undertones. |
| Compound having the structure: 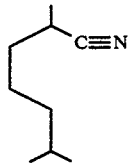 prepared according to Example V, fraction 11. | A sweet, citrus (tart-lemon) cinnamon-like, fatty, lactonic (coconut aroma profile. |
| Compound having the structure: 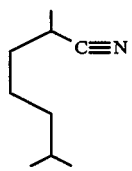 prepared according to Example II, bulked fractions 8-20. | A rhodinol-like, minty, geranium-like profile. |
| Compound having the structure: 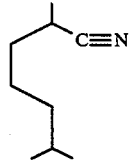 prepared according to Example III, bulked fractions 5-15. | A citrusy, fatty and scorched linen aroma profile. |
| Perfume composition of Example VI(A). | Chypre having orris-like and cinnamon-like topnotes and floral undertone. |
| Perfume composition of Example VI(B). | Chypre having a sweet, citrus (tart-lemon), cinnamon-like, fatty, coconut-like undertone. |
| Perfume composition of Example VI(C). | Chypre having rhodinol-like, minty and geranium-like undertones. |
| Perfume composition of Example VI(D). | Chypre having orris-like and cinnamon-like topnotes and floral, citrusy, fatty and scorched linen undertones. |

EXAMPLE VIII

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table II of Example VII are prepared containing 0.10%, 0.15%, 0.20%, 0.25%, 0.30% and 0.35% of the substance set forth in Table II of Example VII. They are prepared by adding and homogeneously mixing the appropriate quantity of substance set forth in Table II of Example VII in the liquid detergent. The detergents all possess excellent aromas as set forth in Table II of Example VII, the intensity increasing with greater concentrations of substance as set forth in Table II of Exmple VII.

EXAMPLE IX

Preparation of Colognes and Handkerchief Perfumes

Compositions as set forth in Table II of Example VII are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example VII are imparted to the colognes and to the handkerchief perfumes at all levels indicated.

EXAMPLE X

Preparation of Soap Compositions

One hundred grams of soap chips [per sample]-(IVORY ®, produced by the Procter & Gamble Company of Cincinnati, Ohio), are each mixed with one gram samples of substances as set forth in Table II of Example VII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example VII.

EXAMPLE XI

Preparation of Solid Detergent Compositions

Detergents are prepared using the following ingredients according to Example I of Canadian Patent No. 1,007,948:

| Ingredient | Percent by Weight |
| --- | --- |
| "NEODOL ® 45-11 (a $C_{14}$-$C_{15}$ alcohol ethoxylated with 11 moles of ethylene oxide | 12 |
| Sodium carbonate | 55 |
| Sodium citrate | 20 |
| Sodium sulfate, water brighteners. | q.s. |

This detergent is a phosphate-free detergent. Samples of 100 grams each of this detergent are admixed with 0.10, 0.15, 0.20 and 0.25 grams of each of the substances as set forth in Table II of Example VII. Each of the detergent samples has an excellent aroma as indicated in Table II of Example VII.

EXAMPLE XII

Utilizing the procedure of Example I at column 15 of U.S. Pat. No. 3,632,396, non-woven cloth substrates useful as dry-added fabric softening articles of manufacture are prepared wherein the substrate, the substrate coating and the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{20-22}$ HAPS
   22%—isopropyl alcohol
   20%—antistatic agent
   1%—of one of the substances as set forth in Table II of Example VII.

Fabric softening compositions prepared according to Example I at column 15 of U.S. Pat. No. 3,632,396 having aroma characteristics as set forth in Table II of Example VII, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate. One of the substances of Table II of Example VII is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said dryer-added fabric softener non-woven fabrics and these aroma characteristics are described in Table II of Example VII.

EXAMPLE XIII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following ingredients are added to the PVP/VA alcoholic solution:

| Ingredients | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example VII. | 0.10 |

The perfuming substances as set forth in Table II of Example VII add aroma characteristics as set forth in Table II of Example VII which are rather intense and aesthetically pleasing to the users of the soft-feel, good-hold pump hair sprays.

EXAMPLE XIV

Conditioning Shampoos

Monamid CMA (prepared with the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation.

The resulting material is then mixed and cooled to 45° C. and 0.3 weight percent of perfuming substance as set forth in Table II of Example VII is added to the mixture. The resulting mixture is cooled to 40° C. and blending is carried out for an additional one hour in each case. At the end of this blending period, the resulting material has a pleasant fragrance as indicated in Table II of Example VII.

EXAMPLE XV

Four drops of each of the substances set forth in Table II of Example VII, supra, is added separately to two grams of AROMOX® DMC-W to produce a clear premix. The clear premix is added to 200 grams of CLOROX® with stirring resulting in a clear stable, single phase solution. Sufficient 1M aqueous NaOH is added to bring the pH of the mixture up to 12.8. The solution remains substantially stable at 120° F. for a period of seven days. When the 5% aqueous sodium hypochlorite solution is used as a laundry bleach, the resulting laundry, on dry-out in an atmosphere of 65% relative humidity yields substantially no characteristic "hypochlorite" odor, but does have a faint pleasant aroma as set forth in Table II of Example VII. Furthermore, no such characteristic "hypochlorite" aroma is retained on the hands of the individual handling such laundry in both the wet and the dry states.

EXAMPLE XVI

AROMOX® DMMC-W in various quantities is mixed with 0.1 grams of one of the substances set forth in Table II of Example VII, supra. The resulting premixes are then added to 200 grams of an aqueous 5% sodium hypochlorite solution. Sufficient 12.5M aqueous NaOH is added to bring the pH of the mixture up to 13. The following results are obtained:

| Percentage AROMOX® DMMC-W | Clarity of hypochlorite solution after addition of premix |
|---|---|
| 0.23% | Clear after three days |
| 0.15% | Clear after three days |
| 0.08% | Initially slightly turbid; two phases exist after three days. |

When the 5% aqueous sodium hypochlorite solution is used as a laundry bleach, the resulting laundry on dry-out, in an atmosphere of 65% relative humidity, yields substantially no characteristic "hypochlorite" odor, but does have a faint, pleasant aroma as set forth in Table II of Example VII. Furthermore, no such characteristic "hypochlorite" aroma is retained on the hands of the individual handling such laundry in both the wet and dry states.

EXAMPLE XVII

Two grams of AROMOX ® DMMC-W is admixed with eight drops of one of the substances set forth in Table II of Example VII, supra. The premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry, on dry-out in an atmosphere of 50% relative humidity retains a "clean" warm aroma as set forth in Table II of Example VII, supra; whereas without the use of the substance set forth in Table II of Example VII, supra, the bleached laundry has a faint characteristic disagreeable "hypochlorite" aroma.

EXAMPLE XVIII

Two grams of AROMOX ® DMMC-W is admixed with eight drops of one of the substance of Table II of Example VII, supra. This premix is then added, with stirring to 200 grams of a mixture containing 4.5% aqueous sodium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains a "clean fresh" warm aroma as set forth in Table II of Example VII, supra; whereas without the use of the substance set forth in Table II of Example VII, supra, the bleached laundry has a faint characteristic disagreable "hypochlorite" aroma.

EXAMPLE XIX

Two grams of AROMOX ® DMMC-W is admixed with eight drops of one of the substances as set forth in Table II of Example VII, supra. This premix is then added with stirring to 200 grams of a mixture containing 4.5% aqueous sodium hypochlorite and 4.5% aqueous lithium hypochlorite. Sufficient 2M aqueous NaOH is added to bring the pH of the solution to 13.4. The mixture is then heated to 110° F. and maintained at that temperature with stirring for a period of 2 weeks. The resulting solution remains clear as a single phase when used as a laundry bleach. The resulting laundry bleach, on dry-out in an atmosphere of 50% relative humidity, retains an aroma as set forth in Table II of Example VII, supra, whereas without the use of the substance set forth in Table II of Example VII, supra, the bleached laundry has a faint characteristic disagreeable "hypochlorite" aroma.

EXAMPLE XX

Four drops of one of the substances set forth in Table II of Example VII, supra, is added to 1.5 grams of AROMOX ® to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm, long-lasting aroma as set forth in Table II of Example VII, supra. Furthermore, no such characteristic "hypochlorite" aroma is retained on the hands of the individual handling such laundry in both the wet and dry states.

EXAMPLE XXI

Four drops of one of the substances set forth in Table II of Example VII, supra, is added to 1 gram n-undecyl dimethyl amine oxide to produce a clear premix. The clear premix is added to 200 grams of CLOROX ® with stirring resulting in a clear stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" odor but does have a faint pleasant warm aroma as set forth in Table II of Example VII, supra. Furthermore, no such characteristic "hypochlorite" aroma is retained on the hands of the individual handling such laundry in both the wet and the dry states.

EXAMPLE XXII

Four drops of one of the substances as set forth in Table II of Example VII, supra are added to 1 gram of n-dodecyl dimethyl amine oxide to produce a clear premix. The clear premix is added to 200 grams of CLOROX ® with stirring resulting in a clear, stable single phase solution. Sufficient 1M aqueous NaOH is added to bring the pH of the mixture up to 12.8. The solution remains substantially stable at 120° F. for a period of 7 days. When the 5% aqueous sodium hypochlorite solution is used as a laundry bleach, the resulting laundry on dry-out in an atmosphere of 65% relative humidity yields substantially no characteristic "hypochlorite" aroma, but does have a warm, pleasant, long-lasting aroma as set forth in Table II of Example VII, supra. Furthermore, no such characteristic "hypochlorite" aroma is retained on the hands of the individual handling such laundry in both the wet and dry states.

EXAMPLE XXIII

One gram of n-tridecyl dimethyl amine oxide is admixed with eight drops of one of the substances as set forth in Table II of Example VII, supra. This premix is then added with stirring to 200 grams of a 7% aqueous solution of lithium hypochlorite. Sufficient 3M aqueous LiOH is added to bring the pH of the solution to 13.4. The mixture is then heated to 120° F. and maintained at that temperature with stirring for a period of one week. The resulting solution remains clear in a single phase. When used as a laundry bleach, the resulting bleached laundry on dry-out in an atmosphere of 50% relative humidity retains a warm, fresh aroma described in Table II of Example VII, supra, whereas without the use of one of the substances of Table II of Example VII, supra, the bleached laundry has a faint characteristic disagreeable "hypochlorite" aroma.

EXAMPLE XXIV

One gram of DOWFAX ® 3B2; one gram of DOWFAX ® 2A1 (see notes 1 and 2 below) and 0.25 grams of AROMOX ® DMMC-W is admixed with eight drops of one of the compounds of Table II, Example VI. This premix is then added, with stirring to 200 grams of a mixture containing 4.5% aqueous sodium hypochlorite and 4.5% aqueous lithium hypochlorite. Sufficient 4M aqueous LiOH is added to bring the pH of the solution to 13.4. The mixture is then heated to 120° F. and maintained at that temperature for a period of one week. The resulting solution remains clear in a single phase. When used as a laundry bleach, the resulting bleached laundry on dry-out in an atmosphere of 50% relative humidity retains an aroma as set forth in Table II of Example VII; whereas without the use of the material set forth in Table II of Example VII the bleached laundry as a faint characteristic disagreeable "hypochlorite" aroma.

Note 1: DOWFAX ® 2A1 is a material consisting essentially of a mixture of compounds defined according to the structure:

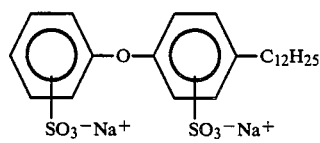

wherein the $C_{12}H_{25}$ moiety is branched chain and the $SO_3^-Na^+$ moieties are at various positions on each of the benzene rings.

Note 2: DOWFAX ® 3B2 is a mixture of compounds essentially defined according to the structure:

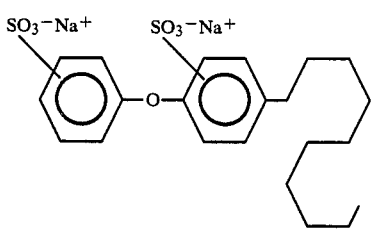

wherein the $SO_3$—$Na^-$ moieties are at various positions on the phenyl moieties. DOWFAX ® 3B2 is a registered trademark of the Dow Chemical Company of Midland, Mich.

Note 3: AROMOX ® DMMC-W is a 30% aqueous solution of dimethyl cocoamine oxide produced by Armac Division of Akzo of Chicago, Ill.

What is claimed is:

1. A product produced according to the process of hydrogenating eucalyptus citriodora in the presence of a palladium-containing catalyst in order to yield a hydrogenated eucalyptus citriodora containing the compound having the structurre:

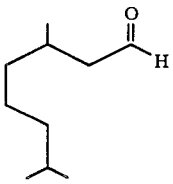

then reacting the thus hydrogenated eucalyptus citriodora with a hydroxylamine salt having the structure:

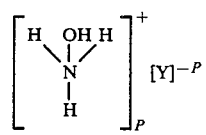

wherein Y represents an anion and P is 0 or 1 thereby forming an oxime salt composition; then reacting the thus-formed oxime salt composition with a base thereby forming an oxime composition containing the compound having the structure:

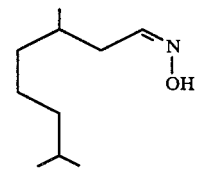

then reacting the thus-formed oxime-containing composition with a dehydrating reagent thereby forming a nitrile-containing composition containing the nitrile having the structure:

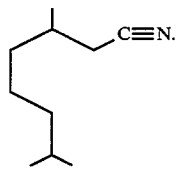

2. A process for augmenting or enhancing the aroma of a consumable material selected from the group consisting of perfume compositions, perfumed articles and perfumed polymers comprising the step of intimately admixing with said consumable material, an aroma augmenting or enhancing quantity of the product defined according to claim 1.

3. A chlorine-containing bleach composition comprising:
   (a) a chlorine bleach base; and
   (b) intimately admixed therewith the product defined according to claim 1.

4. A perfumed aqueous alkali metal hypochlorite solution comprising as a sole detergent a composition of matter selected from the group consisting of (1) at least one substance defined according to the structure:

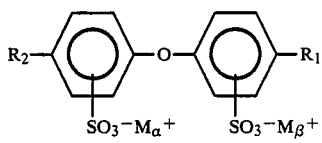

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl and the other of $R_1$ or $R_2$ is hydrogen; wherein $M_\alpha$ and $M_\beta$ are the same or different and each represents alkali metal selected from the group consisting of sodium, potassium and lithium and (2) a mixture comprising a material having the structure:

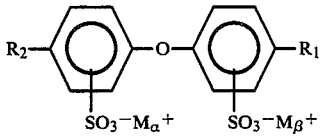

and intimately admixed therewith a substance having the structure:

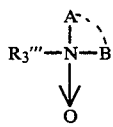

wherein $R_3'''$ is straight chain alkyl; wherein more than 55% of the $R_3'''$ moieties consist of straight chain alkyl having from 11 up to 13 carbon atoms and wherein "A" and "B" are each separately methyl up to 0.2% of one or more compatible perfume oils, said hypochlorite solution having a pH of 11 up to 14.0 and an aroma augmenting or enhancing quantity of the product defined according to claim 1.

5. The composition of matter of claim 4 which is thickened using a thickening quantity of $C_{10}$–$C_{20}$ alkanoic acid salt thickener in a concentration such that the viscosity of the composition is 20–60 centipoises at a temperature of 20°–40° C.

6. The composition of claim 4 wherein the compound having the structure:

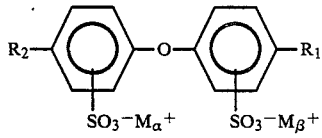

is selected from the group of materials having the structures;

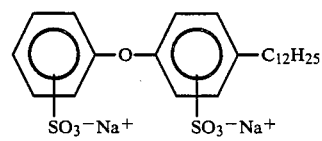

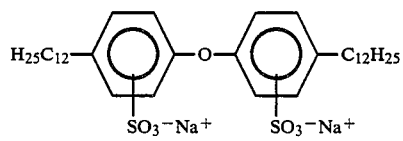

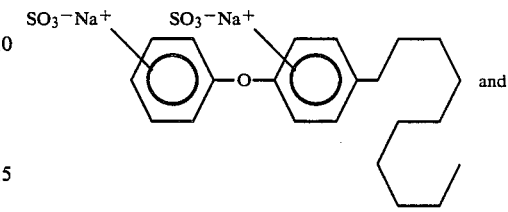

and

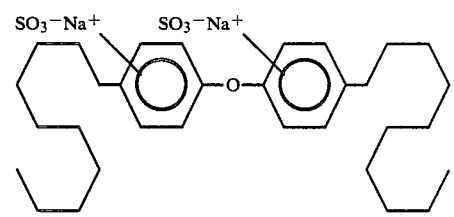

7. A process for augmenting or enhancing the aroma of a consumable material selected from the group consisting of perfume compositions, perfumed articles and perfumed polymers comprising the step of intimately admixing with said consumable material, an aroma augmenting or enhancing quantity of at least one dimethyl substituted alkyl nitrile defined according to the structure:

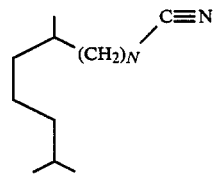

wherein N represents 0 or 1.

8. The process of claim 7 wherein the dimethyl substituted alkyl nitrile has the structure:

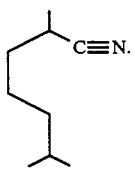

9. The process of claim 7 wherein the dimethyl substituted alkyl nitrile has the structure:

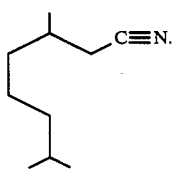

10. A chlorine-containing bleach composition comprising:
(a) a chlorine bleach base; and
(b) intimately admixed therewith at least one compound defined according to the structure:

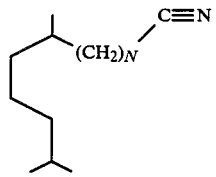

wherein N represents 0 or 1.

11. A perfume aqueous alkali metal hypochlorite solution comprising as a sole detergent a composition of matter selected from the group consisting of (1) at least one substance defined according to the structure:

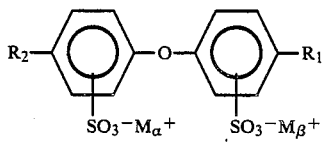

wherein at least one of $R_1$ and $R_2$ is $C_{10}$–$C_{12}$ straight chain or branched chain alkyl; when one of $R_1$ or $R_2$ is $C_{10}$–$C_{12}$ straight chain or branched chain alkyl and the other of $R_1$ or $R_2$ is hydrogen; wherein $M_\alpha$ and $M_\beta$ are the same or different and each represents alkali metal selected from the group consisting of sodium, potassium and lithium and (2) a mixture comprising a material having the structure:

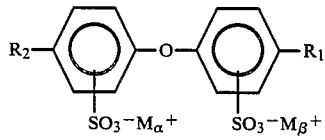

and intimately admixed therewith a substance having the structure:

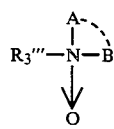

wherein $R_3'''$ is straight chain alkyl; wherein more than 55% of the $R_3'''$ moieties consist of straight chain alkyl having from 11 up to 13 carbon atoms and wherein "A" and "B" are each separately methyl up to 0.2% of one or more compatible perfume oils, said hypochlorite solution having a pH of 11 up to 14.0 and an aroma augmenting or enhancing quantity of at least one compound defined according to the structure:

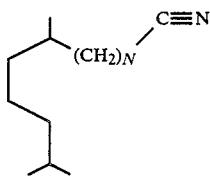

wherein N is 0 or 1.

12. The composition of matter of claim 11 which is thickened using a thickening quantity of $C_{10}$–$C_{20}$ alkanoic acid salt thickener in a concentration such that the viscosity of the composition is 20–60 centipoises at a temperature of 20°–40° C.

13. The composition of claim 11 wherein the compound having the structure:

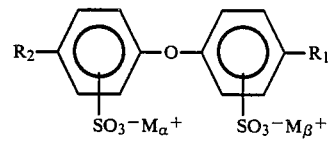

is selected from the group of materials having the structures;

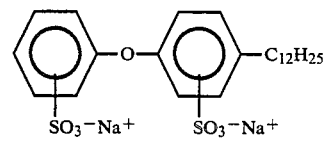

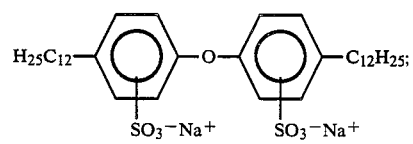

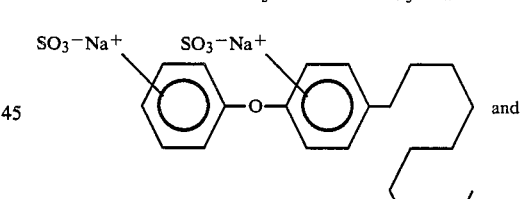

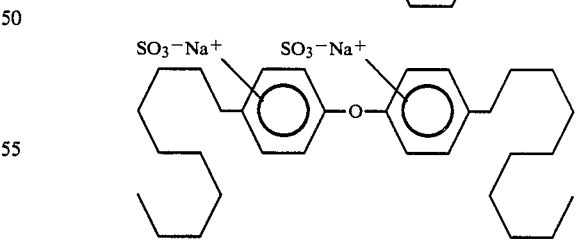

14. The composition of claim 10 wherein N is 0.
15. The composition of claim 10 wherein N is 1.
16. The composition of claim 11 wherein N is 0.
17. The composition of claim 11 wherein N is 1.

* * * * *